(12) United States Patent
    Sood et al.

(10) Patent No.: US 10,987,440 B1
(45) Date of Patent: Apr. 27, 2021

(54) ULTRAVIOLET PATHOGEN DISINFECTION SYSTEM

(71) Applicant: EnviroProcess Consultants, Inc., Rancho Palos Verdes, CA (US)

(72) Inventors: Anurag Sood, Rancho Palos Verdes, CA (US); Neeraj R. Chaudhary, Fremont, CA (US); Sandeep Seth, Houston, TX (US); Danish S. Khatri, Redondo Beach, CA (US)

(73) Assignee: EnviroProcess Consultants, Inc., Rancho Palos Verdes, CA (US)

( * ) Notice: Subject to any disclaimer, the term of this patent is extended or adjusted under 35 U.S.C. 154(b) by 0 days.

(21) Appl. No.: 16/930,100

(22) Filed: Jul. 15, 2020

Related U.S. Application Data

(63) Continuation of application No. 16/926,327, filed on Jul. 10, 2020.

(51) Int. Cl.
    *A61L 2/10* (2006.01)
    *H05B 47/115* (2020.01)
    (Continued)

(52) U.S. Cl.
    CPC .................. *A61L 2/10* (2013.01); *A61L 2/24* (2013.01); *G02B 27/0977* (2013.01);
    (Continued)

(58) Field of Classification Search
    CPC ....................................................... A61L 2/10
    See application file for complete search history.

(56) References Cited

U.S. PATENT DOCUMENTS 6,159,260 A  12/2000  Hammes
6,656,424 B1 12/2003  Deal
(Continued)

FOREIGN PATENT DOCUMENTS

AU   2020100356    5/2020
CN    201629776   10/2010
(Continued)

OTHER PUBLICATIONS

Scientific Air Management—Engineering Air for a Cleaner Environment, https://scientificairmanagement.com, Accessed Approximately May 1, 2020.
(Continued)

*Primary Examiner* — Donald R Spamer
(74) *Attorney, Agent, or Firm* — C. Tumey Law Group PLLC

(57) ABSTRACT

A pathogen disinfection system includes a base and a pathogen disinfection apparatus having a UV light source disposed in the base and configured to emit UV light to at least partially inactivate pathogens exposed to the emitted UV light. Further, the system includes a beam shaping mechanism configured to shape a path of the emitted UV light so that the UV light is confined to a selected width, a first motion sensor configured to detect when an object or human being has moved into the UV light path and send a first signal in response to detecting such a movement, a proximity sensor configured to detect when a human being is present and send a second signal in response to detecting such a presence, and a controller to activate the UV light source after receiving the first signal and deactivating the UV light source after receiving the second signal.

20 Claims, 15 Drawing Sheets

(51) Int. Cl.
   *H05B 47/18* (2020.01)
   *A61L 2/24* (2006.01)
   *G02B 27/09* (2006.01)
(52) U.S. Cl.
   CPC ............ *H05B 47/115* (2020.01); *H05B 47/18* (2020.01); *A61L 2202/11* (2013.01); *A61L 2202/14* (2013.01)

(56) References Cited

U.S. PATENT DOCUMENTS

| | | | |
|---|---|---|---|
| 7,834,335 | B2 | 11/2010 | Harmon et al. |
| 8,067,750 | B2 | 11/2011 | Deal |
| 8,105,532 | B2 | 1/2012 | Harmon et al. |
| 8,999,237 | B2 | 4/2015 | Tumanov |
| 9,345,798 | B2 | 5/2016 | Trapani |
| 9,603,960 | B2 | 3/2017 | Dobrinsky et al. |
| 9,666,424 | B1 | 5/2017 | Veloz et al. |
| 9,907,871 | B2 | 3/2018 | Kreiner et al. |
| 10,111,976 | B2 | 10/2018 | Deshays et al. |
| 10,232,067 | B2 | 3/2019 | Kim et al. |
| 10,265,540 | B2 | 4/2019 | Yehezkel |
| 10,307,504 | B2 | 6/2019 | Munn |
| 10,406,254 | B2 | 9/2019 | Garner et al. |
| 10,413,624 | B2 | 9/2019 | Cole et al. |
| 10,485,887 | B2 | 11/2019 | Ramanand et al. |
| 10,511,341 | B2 | 12/2019 | Lambert et al. |
| D884,129 | S | 5/2020 | Hammes et al. |
| 2002/0146343 | A1 | 10/2002 | Jenkins et al. |
| 2005/0058584 | A1 | 3/2005 | Shyu |
| 2006/0104858 | A1* | 5/2006 | Potember ................ F24F 3/166 422/4 |
| 2006/0216193 | A1* | 9/2006 | Johnson ............... A61N 5/0624 422/24 |
| 2007/0248342 | A1 | 10/2007 | Tamminen |
| 2009/0035177 | A1 | 2/2009 | McEllen |
| 2009/0011700 | A1 | 5/2009 | First et al. |
| 2009/0129974 | A1 | 5/2009 | McEllen |
| 2010/0102252 | A1* | 4/2010 | Harmon .................... A61L 9/20 250/492.1 |
| 2011/0024647 | A1 | 2/2011 | Hsu |
| 2012/0282135 | A1 | 11/2012 | Trapani |
| 2013/0148099 | A1 | 6/2013 | Stautmeister |
| 2013/0277574 | A1* | 10/2013 | Dayton ..................... A61L 2/10 250/455.11 |
| 2016/0036952 | A1 | 2/2016 | Kim et al. |
| 2016/0089458 | A1 | 3/2016 | Liao et al. |
| 2016/0093412 | A1 | 3/2016 | Liao |
| 2016/0106873 | A1 | 4/2016 | Dobrinsky et al. |
| 2017/0080251 | A1 | 3/2017 | Yehezkel |
| 2017/0112954 | A1 | 4/2017 | Dayton |
| 2017/0129396 | A1 | 5/2017 | Salter |
| 2017/0216466 | A1 | 8/2017 | Dujowich et al. |
| 2017/0296686 | A1* | 10/2017 | Cole ........................ A61L 2/10 |
| 2019/0001930 | A1 | 1/2019 | Dellock et al. |
| 2019/0076558 | A1 | 3/2019 | Zhang-Miske |
| 2020/0147249 | A1 | 5/2020 | Hussein et al. |
| 2020/0215213 | A1 | 7/2020 | Bryant et al. |
| 2020/0217450 | A1 | 7/2020 | Fabec |

FOREIGN PATENT DOCUMENTS

| | | |
|---|---|---|
| CN | 109611962 | 4/2019 |
| EP | 3457035 | 2/2020 |
| ES | 2765749 | 6/2020 |
| KR | 20200042418 | 4/2020 |
| WO | 2007084145 | 7/2007 |

OTHER PUBLICATIONS

IQAir—Explore the air quality anywhere in the world, https://www.iqair.com/us, Accessed Approximately May 2020.
KAPSULE Sanitizer—Clinically Proven Results, https://www.kapsuleuv.com, Accessed Approximately May 2020.
Krypton Disinfection Lighting—FAR UV Technologies, https://www.faruv.com/product, Accessed Approximately May 2020.
Adam Kress, Honeywell to introduce fast—affordable ultraviolet cleaning system for airplane cabins, https://www.honeywell.com/en-us/newsroom/pressreleases/2020/06/honeywell-to-introduce-fast-affordable-ultraviolet-cleaning-system-for-airplane-cabins, Accessed Approximately Jun. 2020.
CleanUV Ultraviolet Technology—Waveform Lighting, LLC. https://www.waveformlighting.com/uv-c-led, Accessed Approximately May 2020.
UV-C Surface Disinfecting System—Pearlsurface, https://www.boselec.com/product-category/uv-c-surface-disinfecting-system-pearlsurface/, Accessed May 1, 2020.
UV-C Boston Electronics—Detect, Measure, Control , https://www.boselec.com, Accessed Approximately May 2020.
Create a memorable experience—UV-C LED Philips Airports 254nm, https://www.lighting.philips.com/main/systems/application-areas/airports, Accessed Approximately May 2020.
Care222® Filtered Far UV-C Excimer Lamp Module, https://www.ushio.com/study-shows-ushios-care222-lamps-effectively-inactivate-sars-cov-2-the-covid-19-virus/, Accessed Approximatelty Apr. 2020.
Kenneth Chang, Scientists Consider Indoor Ultraviolet Light to Zap Coronavirus in the Air, https://www.nytimes.com/2020/05/07/science/ultraviolet-light-coronavirus.html, Accessed Approximately, May 2020.
Thin 222nm UV Lamps from Eden Park, http://www.edenpark.com/products.html, Accessed Approximately May 2020.
ProPhotonix UV-B LED curing 320+ nm, https://www.prophotonix.com/applications/uvcuring/, Accessed Approximately May 2020.
AmericanUV DoseCards, https://www.americanultraviolet.com/uv-germicidalsolutions/ pharmacy-laboratory-surface.cfml, Accessed Approximately May 2020.
Xiton Germany UVC Lasers, Our products—perfection of technology, https://xiton-photonics.com/products/, Accessed Approximately May 2020.
UV EXCIMER & XEFL Lamps, Ushio 172nm 230nm, https://www.ushio.com/files/catalog/uvir/uvir-excimer-xefl.pdf, Accessed Approximately May 2020.
UV-V lighting has the power to disinfect the air, surfaces and water, https://www.signify.com/global/ourcompany/blog/innovation/uv-c-radiation-disinfection, Accessed Approximately Jun. 2020.
Sam Shead, Signify plans production hike of UV light that breaks down coronavirus particles in seconds, https://www.cnbc.com/2020/07/24/signify-uvc-coronavirus.html, Accessed Approximately Jul. 2020.
Vishal Mathur, Philips UV-C Disinfection System Review: This Will Disinfect Everything You Can Fit Inside It, https://www.news18.com/news/tech/philips-uv-c-system-review-this-will-disinfect-everything-you-canfit-inside-it-2731485.html, Accessed Approximately Jul. 2020.
Signify/Philips Upper Room Air GLA, http://en.gla-uvc.nl/, Accessed Approximately Jul. 2020.
Cartoni UV-C Boxer—UV disinfection device for video & motion picture equipment, https://www.newsshooter.com/2020/07/27/cartoni-uv-c-boxer-uv-disinfection-device-for-video-motion-picture-equipment/, Accessed Approxiamtely Jul. 2020.
Xenex hospital germicidal—Destroy Deadly Pathogens to improve Safety, https://www.xenex.com/, Accessed Approximately Jun. 2020.
Healthe—UV Light for Sensitization, https://healthelighting.com/pages/sanitization-science, Accessed Approximately Jun. 2020.
Matt Witkowski, UV Angel Announces Two New UV-C Light Products to Neutralize Pathogens on Surfaces and in the Air, https://www.prnewswire.com/news-releases/uv-angel-announces-two-new-uv-c-light-products-to-neutralize-pathogens-on-surfaces-and-in-the-air-301044514.html, Accessed Approximately Jun. 2020.
Robot, UV-C light technology keeping surfaces clean at Greater Boston Food Bank, https://www.wcvb.com/article/robot-uv-c-light-technology-keeping-surfaces-clean-at-greater-boston-food-bank/32999633, Accessed Approximately Jul. 2020.
China Fights Virus With Ultraviolet Light, https://www.courthousenews.com/china-fights-virus-with-ultraviolet-light/, Accessed Approximately Apr. 2020.

(56) References Cited

OTHER PUBLICATIONS

Zhao Shiyue, Can ultraviolet light kill the novel coronavirus? (~Apr. 10, 2020): available at https:/www.chinadaily.com.cn/a/202003/04/WS5e5ee878a31012821727c0f4.html?fbclid=IwAR0HSVznpi6Y3xb96gVytUflx4Vr6rLw2pQOJP3CdW6IXg3LIX8cYR1AYTw, Accessed Approximately Apr. 2020.

Femke Megens, How lamps with UV-C radiation can help reduce health risks, https://www.signify.com/global/our-company/blog/innovation/uv-c-radiation-disinfection, Accessed Approximately Apr. 2020.

Life in a new light, https://sterilray.com/, Accessed Approximately May 2020.

UV Sanitizing Devices, https://toolklean.com/collections/products, Accessed Approximately Jul. 2020.

Newport MKS Deuterium UV-C, https://www.mksinst.com/b/newport, Accessed Approximately May 2020.

Stand-Alone UV-C LEDs vs. Advanced UV-C LED System by AquiSense, https://www.aquisense.com/uv-led-system-design?gclid=CjwKCAjwydP5BRBREiwA-qrCGufdGWYHH_Meyjdh1Ly1mLDAyjAZZ0XU8wOlg0Y3syP0E3hTV7wCFxoC7zYQAvD_BwE, Accessed Approximately May 2020.

Inovative UV LED Solutions, https://phoseon.com/, Accessed Approximately May 2020.

Application of Omega Optical Filters, https://www.omegafilters.com/, Accessed Approximately May 2020.

Colony Square Installing UVC Lighting in Offices to 'Purify and Destroy Airborne Bio-Contaminants', https://whatnowatlanta.com/colony-square-installing-uvc-lighting-in-offices-to-purify-and-destroy-airborne-bio-contaminants/, Accessed Approximately May 2020.

Osram UVC AirZing, https://www.osram.com/pia/airzing.jsp, Accessed Approximately May 2020.

UV Disinfection is Flourishing—But Companies Need to Be more Cautious, Cleanslate UV Disinfection: https://blog.cleanslateuv.com/2019/03/uv-disinfection-is-flourishing-but-companies-need-to-be-more-cautious/, Accessed Mar. 18, 2019.

Anthony Karcz, 6 UV-C Gadgets to Sanitize everything from phones to water to air, Forbes UVC Devices, https://www.forbes.com/sites/anthonykarcz/2020/07/29/6-uv-c-gadgets-to-sanitize-everything-from-phones-to-water-to-air/#3951e1cf3e9c, Accessed Approximately Jul. 2020.

JetBlue's Snazzy New Ultraviolet Cleaning System, https://onemileatatime.com/jetblue-ultraviolet-cleaning-system/ Accessed Approximately May 2020.

Vystar to Produce RxAir400 UV-C Light Air Purifiers with New Manufacturer, https://www.globenewswire.com/news-release/2020/07/16/2063404/0/en/Vystar-to-Produce-RxAir400-UV-C-Light-Air-Purifiers-with-New-Manufacturer.html, Accessed Approximately Jul. 2020.

Honeywell—All Products, https://www.honeywellstore.com/store/all.asp, Accessed Approximately Jul. 2020.

Haiku, https://www.bigassfans.com/fans/haiku/?utm_expid=.X1kQ7KKeTBe4F9jX-17y4w.0&utm_referrer=, Accessed Approximately Jul. 2020.

Signify plans production hike of UV light that breaks down coronavirus particles in seconds, https://www.cnbc.com/2020/07/24/signify-uvc-coronavirus.html, Accessed Approximately Jul. 2020.

UVC Disinfection Machine Launched, https://www.thehindu.com/news/cities/Hyderabad/uvdisinfectant-machine-launched/article31976706.ece, Accessed Approximately Jul. 2020.

Does UV Light Kill Viruses and Germs?, https://nymag.com/strategist/article/does-uv-light-kill-germs-best-sterilizer.html, Accessed Approximately Jul. 2020.

This MIT robot combats COVID-19 and may soon be in your grocery store, https://finance.yahoo.com/news/this-mit-robot-combats-covid-19-and-may-soon-be-in-your-grocery-store-151702949.html?socsrc=hl-viewer&soc_trk=ma, Accessed Approximately Jul. 2020.

Safe and Healthy UVC Wand, https://www.safeandhealthy.com/, Accessed Approximately May 2020.

Anti-Microbial UVC Light Sanitizers, https://toolklean.com/?gclid=CjwKCAjwydP5BRBREiwAqrCGlzxiGsKDERyrhTS6wp7DQI5HVFuq4s3Qa5ArduJTJBJY65KnuWzvBoCHpcQA vD, Accessed Approximately May 2020.

United adds coronavirus UVC light deaning protocol for pilots as pandemic continues, https://www.foxbusiness.com/money/united-airlines-coronavirus-uvc-light-cleaning-pilots, Accessed Approximately May 2020.

IES Committee Report: Germicidal Ultraviolet (GUV)—Frequently Asked Questions, https://media.ies.org/docs/standards/IES%20CR-2-20-V1a-20200507.pdf, Accessed Approximately May 2020.

Airport using robots, UV light to combat COVID-19, https://www.post-gazette.com/business/development/2020/05/05/Pittsburgh-International-Arport-COVID-19-Carnegie-Robotics/stories/202005050120, article published May 5, 2020.

A renowned design firm unveiled a new concept to overhaul airplane cabins for a post-pandemic world that includes removing cabin dasses and staggering economy seats—take a look, https://www.msn.com/en-us/money/companies/a-renowned-design-firm-unveiled-a-new-concept-to-overhaul-airplane-cabins-for-a-post-pandemic-world-that-indudes-removing-cabin-dasses-and-staggering-economy-seats-%E2%80%93-take-a-look/ss-BB17HfTJ#image=2, Published Aug. 7, 2020.

The Gig Economy Is Failing. Say Hello to the Hustle Economy, https://onezero.medium.com/the-gig-economy-is-failingsay- hello-to-the-hustle-economy-13ae3aa91954, Accessed Approximately Jul. 2020.

John Porter, Samsung's UV sterilizer and wireless charger officially announced globally, https://www.theverge.com/2020/7/7/21315738/samsunguv-sterilizer-wireless-charger-10w-phone-wireless-earbuds-sunglasses-clean-hygiene, Accessed Approximately Jul. 2020.

Jessica Stewart, UVMask Is a Reusable Face Mask That Filters and Sterilizes the Air in Real Time, https://mymodernmet.com/uvmask-kickstarter/?preview id=305339, Accessed Approximately May 2020.

Using UV light to kill coronavirus: The benefits and risks, available at https://www.cnet.com/google-amp/news/can-uv-light-protect-you-from-covid-19/. Accessed Approximately May 2020.

Aerosol and Surface Stability of SARS-CoV-2 as Compared with SARS-CoV-1 (correspondence). N Eng J Med 2020, 382 (16): 1564-1567, https://tinyurl.com/covid-lowUVC01, Accessed Approximately Apr. 2020.

An ultraviolet light may help fight spread of novel coronavirus. ABC News. Apr. 16, 2020., https://tinyurl.com/covid-lowUVCO2, Accessed Approximately Apr. 2020.

The Nobel Prize in Physiology or Medicine 1903. NobelPrize.org. Nobel Media AB 2020 <https://www.nobelprize.org/prizes/medicine/1903/summary/> Accessed Approximately.

The History of UV, Apr. 14, 2020, available at https://tinyurl.com/covid-lowUVC04, Accessed Approximately Apr. 2020.

Tseng, C.-C., & Li, C.-S. (2007). Inactivation of Viruses on Surfaces by Ultraviolet Germicidal Irradiation. Journal of Occupational and Environmental Hygiene, 4(6), 400-405.

Buonanno, M., Randers-Pehrson, G., Bigelow, A. W., Trivedi, S., Lowy, F. D., Spotnitz, H. M., . . . Brenner, D. J. (2013). 207-nm UV Light—A Promising Tool for Safe Low-Cost Reduction of Surgical Site Infections. I: In Vitro Studies. PLoS ONE, 8(10), e76968.

Buonanno, M., Stanislauskas, M., Ponnaiya, B., Bigelow, A. W., Randers-Pehrson, G., Xu, Y., . . . Brenner, D. J. (2016). 207-nm UV Light—A Promising Tool for Safe Low-Cost Reduction of Surgical Site Infections. II: In-Vivo Safety Studies. PLOS ONE, 11(6), e0138418.

Katherine J. Wu, The Flu May Linger in the Air, Just Like the Coronavirus, https://www.nytimes.com/2020/07/14/health/flu-aerosols-coronavirus.html?smid=em-share, Accessed Approximately Jul. 2020.

Darrell, M. E. R., Subbarao, K., Feinstone, S. M., & Taylor, D. R. (2004). Inactivation of the coronavirus that induces severe acute respiratory syndrome, SARS-CoV. Journal of Virological Methods, 121(1), 85-91.

Bedell, K., Buchaklian, A. H., & Perlman, S. (2016). Efficacy of an Automated Multiple Emitter Whole-Room Ultraviolet-C Disinfection System Against Coronaviruses MHV and MERS-CoV. Infection Control & Hospital Epidemiology, 37 (05), 598-599.

(56) References Cited

OTHER PUBLICATIONS

Lowe, et al. N95 Filtering Facepiece Respirator Ultraviolet Germicidal Irradiation (UVGI) Process for Decontamination and Reuse, Apr. 10, 2020, https://www.nebraskamed.com/sites/default/files/documents/covid-19/n-95-decon-process.pdf.
UHC Disinfecting Masks Using Intense UV Light, https://tinyurl.com/covid-lowUVC12, Accessed Approximately Apr. 2020.
Harcourt, J., Tamin, A., Lu, X., Kamili, S., Sakthivel, S. K., Murray, J., . . . Thornburg, N. J. (2020). Severe Acute Respiratory Syndrome Coronavirus 2 from Patient with 2019 Novel Coronavirus Disease, United States. Emerging Infectious Diseases, 26(6).
Catherine Triomphe, Tests show UVC lamps could light the way in virus fight, https://medicalxpress.com/news/2020-05-uvc-lamps-virus.html, Published May 10, 2020.
Buonanno, et al., Germicidal Efficacy and Mammalian Skin Safety of 222-nm UV Light, HHS Public Access, Approximately Accessed Aug. 10, 2017. Author Manuscript.
Buonanno, et al., 207-nm UV Light—A Promising Tool for Safe Low-Cost Reduction of Surgical Site Infections. I: In Vitro Studies, PLOS ONE, Oct. 2013.
ScienceDaily, Ultraviolet LEDs prove effective in eliminating coronavirus from surfaces and, potentially, air and water, https://www.sciencedaily.com/releases/2020/04/200414173251.htm, Accessed Approximately Apr. 2020.
Walt Mills, Killing coronavirus with handeld ultraviolet light may be feasible, https://www.medicalnewstoday.com/articles/could-a-novel-uv-light-device-inactivate-sars-cov-2-on-surfaces, Accessed Approximately Jun. 2020.
Welch, D. Buonanno, M., Grilj, V., Shuryak, I., Crickmore, C., Bigelow, A. W., . . . Brenner, D. J. (2018). Far-UVC light: A new tool to control the spread of airborne-mediated microbial diseases. Scientific Reports, 8(1).
Could a New Ultraviolet Technology Fight the Spread of Coronovirus?, https://news.columbia.edu/ultraviolet-technology-virus-covid-19-UV-light, Accessed Approximately Apr. 2020.
SaifAddin, B. K., Almogbel, A. S., Zollner, C. J., Wu, F., Bonef, B., Iza, M., . . . Speck, J. S. (2020). AlGaN deep-ultraviolet light-emitting diodes grown on SiC substrates. ACS Photonics.
Darnell, M. E. R., Subbarao, K., Feinstone, S. M., & Taylor, D. R (2004). Inactivation of the coronavirus that induces severe acute respiratory syndrome, SARS-CoV. Journal of Virological Methods, 121(1), 85-91.
Kim, S.-J., Kim, D.-K., & Kang, D.-H. (2015). Using UVC Light-Emitting Diodes at Wavelengths of 266 to 279 Nanometers to Inactivate Foodborne Pathogens and Pasteurize Sliced Cheese. Applied and Environmental Microbiology, 82(1), 11-17.
Sagripanti, J.-L., & Lytle, C. D. (2010). Sensitivity to ultraviolet radiation of Lassa, vaccinia, and Ebola viruses dried on surfaces. Archives of Virology, 156(3), 489-494.
Yuhua Jin, Isabel Qamar, Michael Wessely, Aradhana Adhikari, Katarina Bulovic, Parinya Punpongsanon, Stefanie Mueller, Photo-Chromeleon: Re-Programmable Multi-Color Textures Using Photochromic Dyes MIT CSAIL, Cambridge, MA, Published Oct. 2019.
Sara E Beck, Hodon Ryu, Laura A Boczek, Jennifer L Cashdollar, Kaitlyn M Jeanis, James S Rosenblum, Oliver R Lawal, Karl G Linden, Evaluating UV-C LED disinfection performance and investigating potential dual-wavelength synergy, https://pubmed.ncbi.nlm.nih.gov/27889622/, Accessed Approximately May 2020.
Physicsworld, the potential of far-ultraviolet light for the next pandemic, https://physicsworld.com/a/the-potential-of-far-ultraviolet-light-for-the-next-pandemic/, Accessed Approximately May 2020.
Protecting Against Exposure, http://nuclearconnect.org/know-nuclear/science/protecting, Accessed Approximately Jun. 2020.
Answer to Question #9450 Submitted to "Ask the Experts", https://hps.org/publicinformation/ate/q9450.html, Accessed Approximately May 2020.
UV Light That Is Safe for Humans but Bad for Bacteria and Viruses, https://www.genengnews.com/topics/translational-medicine/uv-light-that-is-safe-for-humans-but-bad-for-bacteria-and-viruses/, Accessed Approximately Apr. 2020.
EPA Approves Two Lysol Sprays for Killing Coronavirus on Surfaces, https://www.aarp.org/health/conditions-treatments/info-2020/epa-approves-lysol-coronavirus-surfaces.html, Accessed Approximately May 2020.
Ultraviolet radiation is a strong disinfectant. It may be what our schools, hospitals and airports need, https://theconversation.com/ultraviolet-radiation-is-a-strong-disinfectant-it-may-be-what-our-schools-hospitals-and-airports-need-142277, Accessed Approximately Jul. 2020.
Whole House Fan, http://riderrants.blogspot.com/2020/07/our-familys-secret-weapon-against-covid.html, Accessed Approximately Jul. 2020.
Aboard the Diamond Princess, a Case Study in Aerosol Transmission, https://www.nytimes.com/2020/07/30/health/diamond-princess-coronavirus-aerosol.html?smid=em-share%E2%80%A2, Published Jul. 30, 2020.
Fennelly, K. P., Particle sizes of infectious aerosols: implications for infection control, https://www.thelancet.com/journals/lanres/article/PIIS2213-2600(20)30323-4/fulltext, Accessed Approximately Jul. 2020.
JV Chamary, We Still Don't Know How Long Coronavirus Lasts on Surfaces, https://www.forbes.com/sites/jvchamary/2020/07/31/coronavirus-surface-disinfectants/#7169f2d93402, Accessed Approximately Jul. 2020.
For $1 per person, UV light can help protect world from virus, scientists claim, https://www.timesofisrael.com/for-1-per-person-uv-light-can-help-protect-world-from-virus-scientists-find/, Accessed Approximately Jun. 2020.
What Happens to Viral Particles on the Subway, https://www.nytimes.com/interactive/2020/08/10/nyregion/nyc-subway-coronavirus.html, Published Aug. 10, 2020.
Zhang, Z., Kushimoto, M., Sakai, T., Sugiyama, N., Schowalter, L. J., Sasaoka, C., & Amano, H. (2019). A 271.8 nm deep-ultraviolet laser diode for room temperature operation. Applied Physics Express.
Tour of the Electromagnetic Spectrum—Ultraviolet Waves, https://science.nasa.gov/ems/10_ultravioletwaves, Accessed Approximately Apr. 2020.
Holmes, E. C. (2009). The comparative genomics of viral emergence. Proceedings of the National Academy of Sciences, 107(suppl_1), 1742-1746.
How Long Can the Virus That Causes COVID-19 Live on Surfaces? https://hub.jhu.edu/2020/03/20/sars-cov-2-survive-on-surfaces/, Accessed Approximately Apr. 2020.
Ultraviolet Radiation, https://www.ccohs.ca/oshanswers/phys_agents/ultravioletradiation.html, Accessed Approximately May 2020.
Is UVC Safe?, https://www.klaran.com/is-uvc-safe, Accessed Approximately May 2020.
Coronavirus disease (COVID-19) advice for the public: Mythbusters, https://www.who.int/emergencies/diseases/novel-coronavirus-2019/advice-for-public/myth-busters, Accessed Approximately May 2020.
UV Radiation & Your Skin, https://www.skincancer.org/risk-factors/uv-radiation/, Accessed Approximately May 2020.
Ultraviolet germicidal irradiation, https://en.wikipedia.org/wiki/Ultraviolet_germicidal_irradiation, Accessed Approximately Apr. 2020.
UCI physicists exploring use of Blu-ray disc lasers to kill COVID-19, other viruses, https://news.uci.edu/2020/05/19/uci-physicists-exploring-use-of-blu-ray-disc-lasers-to-kill-covid-19-other-viruses/, Accessed Approximately Apr. 2020.
Navy ACGIH 200-315nm, Apr. 1992, Ultraviolet Radiation Guide. available at https://www.med.navy.mil/sites/nmcphc/Documents/policy-and-instruction/ih-ultraviolet-radiation-technical-guide.pdf.
Electromagentic Spectrum, http://web.mit.edu/cohengroup/safety/uv110720safety.pdf, Accessed ApproximatelyApr. 2020.
Using UV light to kill coronavirus: The benefits and risks, https://www.cnet.com/health/can-uv-light-protect-you-from-covid-19/, Accessed Approximately Jul. 2020.

(56) References Cited

OTHER PUBLICATIONS

Garcia de Abajo, F. J., Hernández, R. J., Kaminer, I., Meyerhans, A., Rosell-Llompart, J., & Sanchez-Elsner, T. (2020). Back to Normal: An Old Physics Route to Reduce SARS-CoV-2 Transmission in Indoor Spaces. ACS Nano.

Narita, K., Asano, K., Morimoto, Y., Igarashi, T., & Nakane, A. (2018). Chronic irradiation with 222-nm UVC light induces neither DNA damage nor epidermal lesions in mouse skin, even at high doses. PLOS One, 13(7), e0201259.

239 Experts With One Big Claim: The Coronavirus Is Airborne, https://www.nytimes.com/2020/07/04/health/239-experts-with-one-big-claim-the-coronavirus-is-airborne.html, Accessed Approximately Jul. 2020.

Zhao, S., Connie, A. T., Dastjerdi, M. H. T., Kong, X. H., Wang, Q., Djavid, M., . . . Mi, Z. (2015). Aluminum nitride nanowire light emitting diodes: Breaking the fundamental bottleneck of deep ultraviolet light sources. Scientific Reports, 5(1).

Does UV light kill the new coronavirus, https://www.livescience.com/uv-light-kill-coronavirus.html, Accessed Approximately Jul. 2020.

Hygiene Theater Is a Huge Waste of Time, https://www.theatlantic.com/ideas/archive/2020/07/scourge-hygiene-theater/614599/, Accessed Approximately Jul. 2020.

Riediker, M., & Tsai, D.-H. (2020). Estimation of Viral Aerosol Emissions From Simulated Individuals With Asymptomatic to Moderate Coronavirus Disease 2019. JAMA Network Open, 3(7), e2013807.

U.S. Appl. No. 16/926,327, filed Jul. 10, 2020.
U.S. Appl. No. 16/930,105, filed Jul. 15, 2020.
U.S. Appl. No. 16/930,109, filed Jul. 15, 2020.
U.S. Appl. No. 16/930,112, filed Jul. 15, 2020.
U.S. Appl. No. 16/930,119, filed Jul. 15, 2020.
Non Final Office Action Summary for U.S. Appl. No. 16/930,105 dated Aug. 20, 2020.
Non Final Office Action Summary for U.S. Appl. No. 16/930,109 dated Aug. 27, 2020.
Non Final Office Action Summary for U.S. Appl. No. 16/930,112 dated Aug. 20, 2020.
Non Final Office Action Summary for U.S. Appl. No. 16/930,119 dated Aug. 20, 2020.
Non Final Office Action Summary for U.S. Appl. No. 16/926,327 dated Aug. 20, 2020.
Big Ass Fans. Tweet from Jul. 9, 2020. (Year: 2020).
California Life HD. Big Ass Fans Unveils Haiku, Featuring UV-C Technology. Jun. 25, 2020. https://www.californialifehd.com/2020/06/25/big-ass-fans-unveils-haiku-featuring-uv-c-technology/ (Year: 2020).
Final Office Action Summary for U.S. Appl. No. 16/930,105 dated Nov. 5, 2020.
Final Office Action Summary for U.S. Appl. No. 16/930,119 dated Nov. 12, 2020.
Final Office Action Summary for U.S. Appl. No. 16/930,112 dated Nov. 25, 2020.
Final Office Action Summary for U.S. Appl. No. 16/930,109 dated Dec. 1, 2020.
Final Office Action Summary for U.S. Appl. No. 16/926,327 dated Dec. 1, 2020.

\* cited by examiner

US 10,987,440 B1

ULTRAVIOLET PATHOGEN DISINFECTION SYSTEM

CROSS-REFERENCE TO RELATED APPLICATION

The present application is a continuation of U.S. patent application Ser. No. 16/926,327, entitled "ULTRAVIOLET PATHOGEN DISINFECTION SYSTEM," filed on Jul. 10, 2020, the disclosure of which is incorporated herein by reference for all purposes.

BACKGROUND

Pathogens such as bacteria, spores, mildew, and viruses generally pose a threat to human health. Exposure to some of these pathogens (e.g., Covid-19 SARS-CoV-2 coronavirus) may cause a person to contract a severe, or in some cases fatal illness. As such, avoiding exposure to some of these pathogens is paramount. Exposure to pathogens generally results from direct contact with a person infected with the pathogen, contacting a surface contaminated with the pathogen, contacting infected droplets in the air resulting from a cough, sneeze, etc., or other forms of transmission. Public areas pose a particularly high risk of exposure as people are generally in closer to proximity to each other such that a person may directly (e.g., handshake) or indirectly (e.g., droplets from cough) be exposed to a person infected with a pathogen. Avoiding these forms of transmission may be facilitated during times of risk (e.g., flu season and pandemics) via social distancing. Unfortunately, practicing social distancing may be impractical in certain situations leaving people at risk is public areas.

Further, another potentially high risk of exposure in public areas may be from contacting contaminated surfaces (e.g., restaurant tables and seating, checkout counters, public transportation seats and rails, card readers, door handles, etc.) as the contaminated surfaces cannot be identified by the naked eye and the surfaces may remain contaminated for hours or days after being contacted by an infected individual. Routine cleaning of hard surfaces (e.g., tables) may mitigate risk, but sufficient cleaning for removing the pathogen from surfaces consistently after contact with every individual may not be reasonable in certain settings. Further, sufficient cleaning of soft surfaces (e.g., cloth seats) is substantially more difficult and not common practice. As such common surfaces in public spaces (e.g., places where people may transmit or become infected with a communicable respiratory infection) may pose a substantially high risk of exposure to individuals. However, society should not have to avoid public spaces and live in perpetual risk of infection.

In the past, people would continue to venture out in society even in times of risk (e.g., flu season). It was generally accepted that some people would occasionally contract illnesses due to pathogens (e.g., influenza, stomach bugs, etc.), but society at large was unaffected. Unfortunately, that has changed in the recent wake up Covid-19. As Covid-19 appears to cause harsher symptoms and poses an unusually high risk of death, at least some public spaces have been shut down for the safety of society. Eventually, people will be permitted to re-enter public spaces. However, an ongoing risk of infection may persist, especially in public spaces. This may cause people to be reluctant to go out into public, which negatively affects society and the economy. For example, even after re-opening, restaurants may see a significant downturn in patrons in comparison to pre-Covid-19 business. To help restore society, a system or method for consistently and more reliably eliminating pathogens from public spaces is needed.

BRIEF DESCRIPTION OF THE DRAWINGS

These drawings illustrate certain aspects of some examples of the present disclosure and should not be used to limit or define the disclosure.

DETAILED DESCRIPTION

Figure 1:
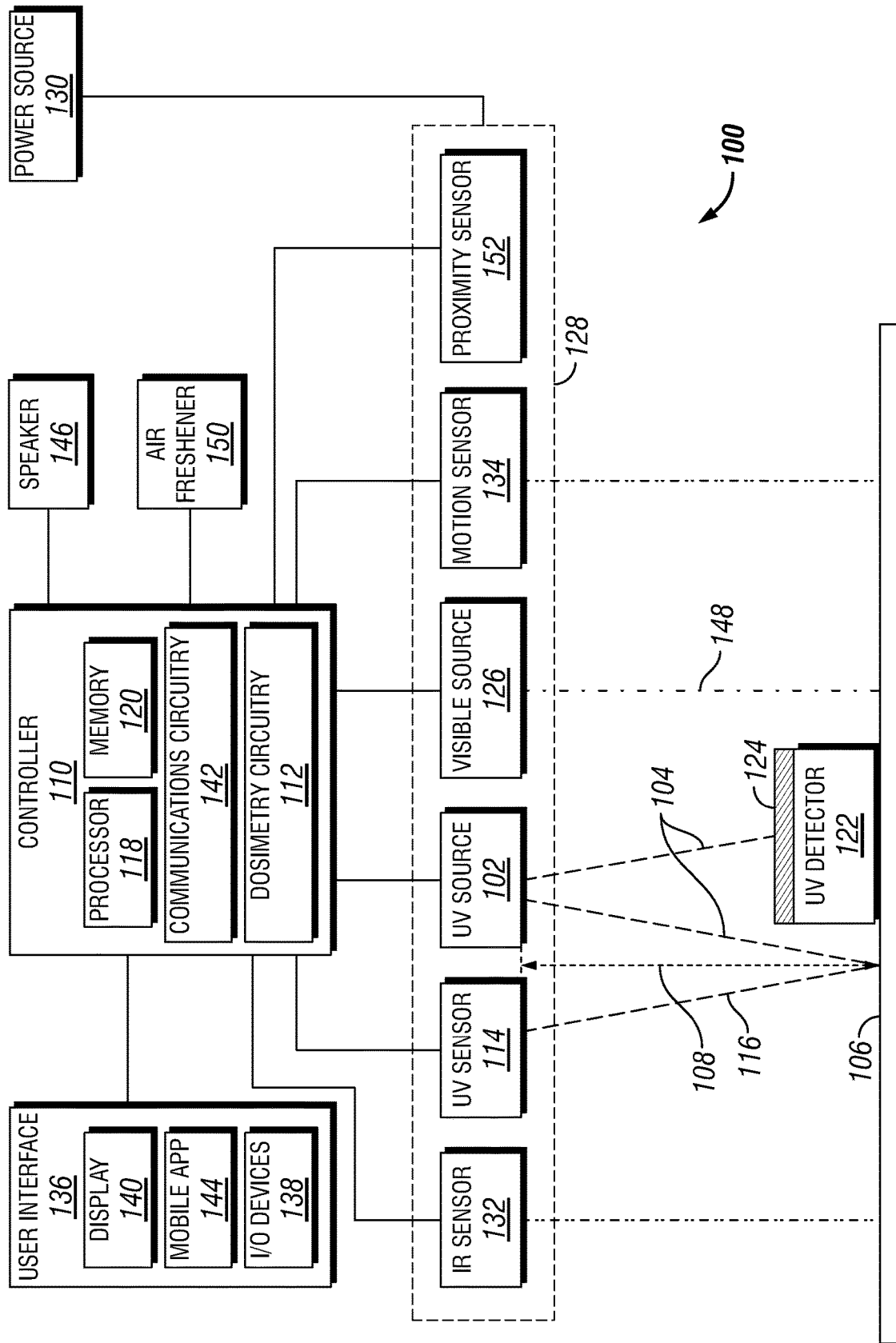
FIG. 1 is a block diagram of an embodiment of an ultraviolet (UV) pathogen disinfection system in accordance with one or more embodiments of the disclosure.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Referring now to the drawings, FIG. 1 is a block diagram of an ultraviolet (UV) disinfection system 100 in accordance with one or more embodiments of the disclosure. As illustrated, the UV disinfection system 100 includes a UV light source 102 configured to emit UV light 104 toward a target location 106 to at least partially inactivate airborne and surface-deposited pathogens at the target location 106. The target location 106 may include a target surface (e.g., tabletop, portable communication device, etc.) or a target ambient air (e.g., location in the ambient air proximate the UV disinfection system). Further, the UV light 104 may be configured to at least partially inactivate pathogens between the UV light source 102 and the target location 106. That is, the UV light 104 may at least partially inactivate any airborne and surface-deposited pathogens exposed to the UV light 104 emitted from the UV light source 102. The UV light source 102 may be configured to operate (e.g., emit the UV light 104) in the presence of people, without any direct exposure to the people.

The UV light source 102 may include a UV light emitting diode (LED), a UV bulb, a scanning UV laser, or any other suitable UV light source 102 for emitting the UV light 104. The UV light source may be a single element or an array of multiple elements, and may include an optical lens and/or mirrors to direct the output energy to a target area or space. While active, the UV light source 102 emits the UV light 104 at a mean peak wavelength range between 200-280 nanometers, which may at least partially inactivate pathogens (e.g., Covid-19 SARS-CoV-2 coronavirus, all known coronaviruses, etc.) at the target location 106. Alternatively, the mean peak wavelength range may be between 200-250 nanometers, 200-220 nanometers, or any other suitable range. In some embodiments, the UV light source 102 may have a narrow bandpass filter. For example, the UV light source 102 may include a ±5 nanometer full width at half maximum (FWHM) bandpass filter.

Moreover, the UV light source 102 may be configured to provide a target dosage of the UV light 104 to the target location 106 to achieve inactivation of the pathogens on the target location 106. The target dosage may include a range of 1-120 millijoule/$cm^2$ of exposure of the target location 106 to the UV light 104. Alternatively, the target dosage may include a range of 1-20 millijoule/$cm^2$. To achieve the target dosage, the UV light source 102 may be configured to emit the UV light 104 at a power of 0.1-150 watts at a distance 108 of 5-300 cm from the target location 106. The actual dosage at the target location 106 may vary based at least in part on the distance 108 between the UV light source 102 and the target location 106. In some embodiments, the UV disinfection system 100 includes a controller 110 having dosimetry circuitry 112 configured to monitor the actual dosage (e.g., cumulative dosage) of the UV light 104 at the target location 106 in real-time based at least in part on an intensity and/or power of the UV light 104, duration, and the distance 108 between the UV light source 102 and the target location 106. The controller may receive a cumulative dose signal indicating the actual dosage. Based on the monitored actual dosage, the controller 110 may be configured to vary an output power of the UV light source 102. For example, the UV light source 102 may move towards the target location 106 such that the actual dosage at the target location 106 increases. Based on the monitored actual dosage, the controller 110 may reduce the output power or shut off the UV light source 102 to achieve the target dosage at the target location 106.

Further, the UV disinfection system 100 may include a UV sensor 114 (e.g., distance sensor) configured to detect UV light 116 reflected from the target location 106 (e.g., target surface). In some embodiments, the UV sensor 114 is configured to output reflected UV light 116 data (e.g., a distance input signal) to the controller 110. Using data from the reflected UV light 116, the controller 110 may be configured to calculate, via an algorithm, the distance 108 between the target location 106 and the UV light source 102. The distance 108 may be calculated in real-time such that the controller 110 may monitor the actual dosage in real-time. The controller 110 may be configured to monitor the actual dosage of the UV light 104 at the target location 106 in real-time via a processor 118 and a memory 120. The processor 118 may include one or more processing devices, and the memory 120 may include one or more tangible, non-transitory, machine-readable media. By way of example, such machine-readable media can include RAM, ROM, EPROM, EEPROM, or optical disk storage, magnetic disk storage or other magnetic storage devices, or any other medium which can be used to carry or store desired program code in the form of machine-executable instructions or data structures and which can be accessed by the processor 118 or by other processor-based devices (e.g., portable communication devices). In some embodiments, the memory 120 is configured to store controller instructions executable by the processor 118 to output various control system signals. For example, the processor 118 may execute the controller instructions to reduce the output power or shut off the UV light source 102 (e.g., send a deactivation signal to the UV light source) when the cumulative dose signal indicates that the target dosage has been achieved.

Moreover, the UV disinfection system 100 may include a UV detector 122 positioned on the target location 106 (e.g. target surface). The UV detector 122 is configured to provide an indication of exposure of the target location 106 to the UV light emitted from the UV light source 102. The UV detector 122 may include a phosphorescent material layer 124 that changes colors in response to exposure to the UV light 104 having the mean peak wavelength between 200-280 nanometers. In some embodiments, the UV detector 122 is configured to gradually change colors based at least in part on the actual dosage of UV light 104 provided to the phosphorescent material layer 124. For example, once 10 percent of the target dosage has been delivered, the phosphorescent material layer 124 may have a red color. At 50 percent of the target dosage (e.g., a midpoint to the target dosage), the phosphorescent material layer 124 may have a yellow color. Further, at completion of the target dosage, in some embodiments, the phosphorescent material layer 124 may have a green color indicating that the target location 106 has been exposed to the target dosage. In some embodiments, the UV detector 122 is configured to revert from the green color back to the red color over time. For example, the phosphorescent material layer 124 of the UV detector 122 may revert from green to red over a period of 10-600 seconds. Moreover, the UV disinfection system 100 may include a visible light source 126 for emitting visible light 148 having a wavelength in the visible light spectrum (e.g., about 380-700 nanometers), with a power draw of 0.1-150 watts. target location The UV disinfection system 100 may include circuitry 128 for providing power (e.g., from a power source 130) to activate the UV light source 102 and/or the visible light source 126. In some embodiments, the circuitry 128 includes a circuit board for housing the UV light source 102 and/or the visible light source 126. For example, if the UV and visible light sources are LEDs and not other bulb types, a UV LED and a visible light LED may be mounted to the circuit board. Alternatively, the circuitry 128 may include an integrated circuit such that the UV light source 102 and/or the visible light source 126 are mounted to the integrated circuit. However, any suitable circuitry 128 may be used for providing power to the UV light source 102 and/or the visible light source 126.

Moreover, as set forth above, the UV disinfection system 100 may include the controller 110 for controlling operation of the UV disinfection system 100. That is, the controller 110 may control activation/deactivation of the UV light source 102 and/or the visible light source 126, as well as power output for the respective light sources 102, 126). Further, the controller 110 may be configured to receive input from a motion sensor to determine a dosage at the target location 106. In some embodiments, the controller 110 may also be configured to receive inputs from other sources (e.g., an infrared sensor 132, a motion sensor 134, a user interface 136, proximity sensor 152, etc.) of the UV disinfection system 100. For example, the controller 110 may be configured to receive temperature data from the infrared sensor 132, or other temperature sensor, configured to detect temperatures within a human or mammalian body temperature range (e.g., 95-105 degrees Fahrenheit) or over 10 degrees Fahrenheit above ambient or actual room temperature and within the UV light beam zone of illumination, such that the controller 110 may determine that a person is within a deactivation zone configured to trigger deactivation of the UV light source 102. Further, the controller 110 may be configured to receive ambient temperature data, weather data, etc. from external sources, which may be used in determining whether the detected temperature is over 10 degrees Fahrenheit above ambient or actual room temperature. In another example, the motion sensor 134 may provide data indicating that a person is within an activation zone configured to trigger activation of the UV light source 102. In some embodiments, the input may include operational data, diagnostics, and maintenance parameters. In some embodiments, the controller 110 may be configured to receive inputs based at least in part on user input via the user interface 136. The user interface 136 may include an input/output device 138 (e.g., keyboard, mouse, or touch screen) configured to provide the user input to the controller 110. Further, the user interface 136 may include a display 140 (e.g., computer monitor or personal device screen) configured to display information related to operation of the UV disinfection system 100 such that a user may monitor operation of the UV disinfection system 100 via a portable communication device, tablet, desktop computer, or any other suitable electronic device.

Moreover, the controller 110 may be configured to receive the inputs, as well as output data, controller instructions, etc., via communications circuitry 142. The communications circuitry 142 may include antennas, radio transceiver circuits, and signal processing hardware and/or software (e.g., hardware or software filters, A/D converters, multiplexers, amplifiers), or a combination thereof, and that may be configured to communicate over wireless communication paths via infrared (IR) wireless communication, satellite communication, broadcast radio, microwave radio, Bluetooth, Zigbee, Wifi, UHF, NFC, etc. In some embodiments, the controller 110 may communication with a mobile application 144 (mobile app) via the communication circuitry 142. For example, the controller 110 may output data to a cloud based mobile app 144 via the communication circuitry 142. Users may access the mobile app 144 via the user interface 136 set forth above.

Further, the controller 110 may be configured to output data in response to predetermined events or triggers for the UV disinfection system 100. For example, the controller 110 may be configured to output a sound signal to a speaker device of the UV disinfection system 100 in response to activation of the UV light source 102. The speaker device 146 may include a local speaker device 146. However, the speaker device 146 may also include a speaker of a device providing access to the user interface 136 (e.g., a portable communication device speaker). The sound signal may be configured to cause the speaker device 146 to output an audio cue to provide an indication that the UV light source 102 is active. The controller 110 may be configured to output other sound signals to the speaker device 146 in response to operation of the UV light source 102, deactivation of the UV light source 102, or any other suitable event or trigger. That is, the speaker device may be configured to produce an audio output in response to activation of the UV light source, before, during, or after activation or deactivation of the UV light. In another example, the controller 110 may be configured to output a signal to an air freshener device 150 based on any suitable event or trigger (e.g., activation of the UV light source). The air freshener device 150 may be configured to output a scented aroma and/or a neutralizing agent in response to activation of the UV light source 102 to provide an indication that the UV light source 102 is active. The neutralizing agent configured to react with and neutralize unwanted byproducts (e.g., ozone, organic, or organochlorine compounds) of UV exposure.

Figure 2:
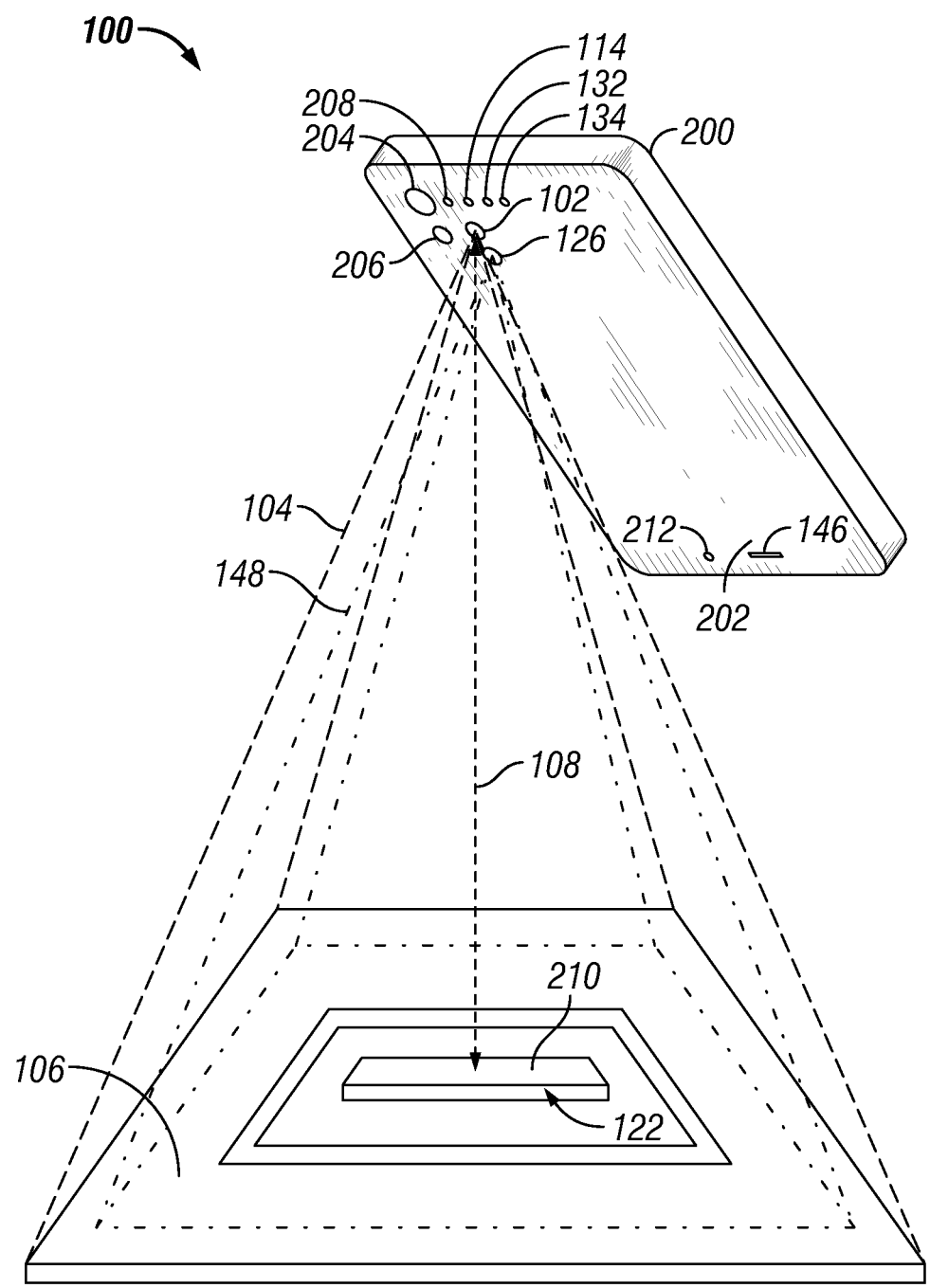
FIG. 2 illustrates a perspective view of the UV disinfection system for a portable communication device, in accordance with one or more embodiments of the disclosure.

FIG. 2 illustrates a perspective view of the UV disinfection system 100 for a portable communication device, in accordance with one or more embodiments of the disclosure. As illustrated, the portable communication device (e.g., mobile device 200) includes the UV light source 102 configured to emit UV light 104 at a mean peak wavelength between 200-280 nanometers toward the target location 106 to at least partially inactivate pathogens at the target location 106. In some embodiments, the mean peak wavelength range may alternatively be between 200-250 nanometers, 200-220 nanometers, or any other suitable range. The UV light source 102 may be disposed on a rear portion 202 of the mobile device 200 proximate a rear camera 204, camera flash 206, microphone 208, etc. However, the UV light source 102 may be disposed on any portion of the mobile device 200. Further, the UV light source 102 may be configured to operate (e.g., emit the UV light 104) in the presence of people, without any direct exposure to the people. For example, a person may hold the mobile device 200 during operation without being directly exposed, or exposing anyone else to the emitted UV light 104.

As set forth above, the UV light source 102 is configured to provide a target dosage of the UV light 104 to the target location 106 to achieve inactivation of the pathogens on the target location 106. For example, the target dosage may include 1-20 millijoule/cm$^2$ of exposure of the target location 106 to the UV light 104. To achieve the target dosage, a user may activate the UV light source 102 while holding the mobile device 200 within 6-18 inches from the target location 106 for a disinfection cycle of 5-60 seconds. For example, the user may activate the UV light source 102 for a disinfection cycle of 10 seconds while holding the mobile device 200 at a distance 108 of about twelve inches from a door handle to at least partially inactivate pathogens on the door handle.

To determine the distance 108 between the mobile device 200 and the target location 106 such that the target dosage may be achieved, the UV disinfection system 100 may include the UV sensor 114 set forth above in FIG. 1. The UV sensor 114 may be disposed on the rear portion of the mobile device 200 proximate the UV light source 102. A least a portion of the UV light 104 emitted from the UV light source 102 may reflect from the target location 106 in a direction toward the UV sensor 114. The UV sensor 114 may be configured to detect the reflected UV light from the target location 106 and output reflected UV data to the controller 110 (e.g., shown in FIG. 1) of the mobile device 200. The mobile device 200 may use the reflected UV light data to calculate the distance 108 between the target location 106 and the UV light source 102. The distance 108 may be calculated in real-time. As set forth above, the actual dosage at the target location 106 may vary based at least in part on the distance 108 between the UV light source 102 and the target location 106. In some embodiments, the UV disinfection system 100 includes dosimetry circuitry 112 (e.g., shown in FIG. 1) configured to monitor the actual dosage (e.g., cumulative dose) of the UV light 104 at the target location 106 in real-time based at least in part on an intensity and/or power of the UV light 104, a duration of exposure to the UV light 104, and the distance 108 between the UV light source 102 and the target location 106. Based on the monitored actual dosage, the mobile device 200 may be configured to vary an output power of the UV light source 102 such that the UV light source 102 provides the target dosage during the disinfection cycle. In lieu of the UV sensor 114, UV disinfection system 100 may include an ultrasound wave emitter and return ultrasound wave sensor as the means by which distance to target location 106 is measured, providing the distance input to dosimetry circuit 112. In any event the UV sensor 114 or other suitable alternative represent a distance measuring device.

The UV pathogen disinfection system may also include the UV detector 122 configured to change colors in response to exposure to UV light 104 to provide an indication of exposure to UV light 104. The UV detector 122 may be detachably mounted to the mobile device 200 or a mobile device 200 case secured to the mobile device 200. Prior to operation of the UV disinfection system 100, a user may detach the UV detector 122 from the mobile device 200 and/or case and place the UV detector 122 under, behind, or otherwise proximate to the target location 106 (e.g., the object to be disinfected). The UV detector 122 is configured to provide an indication in response to exposure to UV light 104. That is the UV detector 122 is configured to change colors from a first color to a second color in response to exposure to UV light 104. For example, the UV detector 122 may change from a red color to a green color in response to exposure to the UV light 104. The UV detector 122 may include a surface 210 having phosphorescent and/or photochromic material configured to change color under the UV light 104 having the mean peak wavelength between 200-280 nanometers. The UV detector 122 may be configured to provide the indication (e.g., change color) based on exposure to the UV light 104 from the UV light source 102. The UV detector 122 may fully provide the indication after being exposed to the target dosage. For example, the UV detector 122 may change from a red color to a green color upon being exposed to the target dosage. In some embodiments, the UV detector 122 is configured to revert from the second color to the first color within 10-60 seconds after exposure to the UV light 104 ceases. For example, the UV detector 122 may revert from the green color back to the red color after 10 seconds.

The UV disinfection system 100 may also include a temperature sensor (e.g., the infrared sensor 132) configured to monitor the temperature proximate the target location 106 and output temperature data to the controller 110. In some embodiments, the UV disinfection system may include the motion sensor 134 configured to monitor motion proximate the target location 106 and output motion data to the controller 110. Based at least in part on the temperature data and/or motion data, the controller 110 may determine whether a person is disposed in a path of the UV light 104 emitted from the UV light source 102. In response to detecting a person in the path of the UV light 104, the controller 110 may output a deactivation signal to deactivate the UV light source 102. In some embodiments, the UV light source 102 may automatically re-activate in response to the controller 110 determining that the person is no longer in the path of the UV light 104. Alternatively, the mobile device 200 may require manual re-activation of the UV light source 102. Further, in response to detecting a person in the path of the UV light 104, the controller 110 may also output a warning sound signal configured to provide an audio cue to the user that the UV light source 102 has been deactivated in response to detecting a person in the path of the UV light source 102.

As illustrated, the UV disinfection system 100 may further include the visible light source 126 configured to emit the visible light 148. The visible light source 126 may include the camera flash 206 of the mobile device 200. However, the visible light source 126 may include a separate, dedicated LED or other light bulb for providing the normal light. Any suitable visible light source 126 arrangement may be incorporated. Moreover, in some embodiments, the UV disinfection system 100 includes the speaker device 146 configured to emit an audible sound, before, during, or after activation or deactivation of the UV light source 102, or some combination thereof. Further, in some embodiments, the UV disinfection system may include a tilt sensor 212 configured to provide a tilt angle signal indicating a tilt angle of the mobile device 200.

Figure 3A:
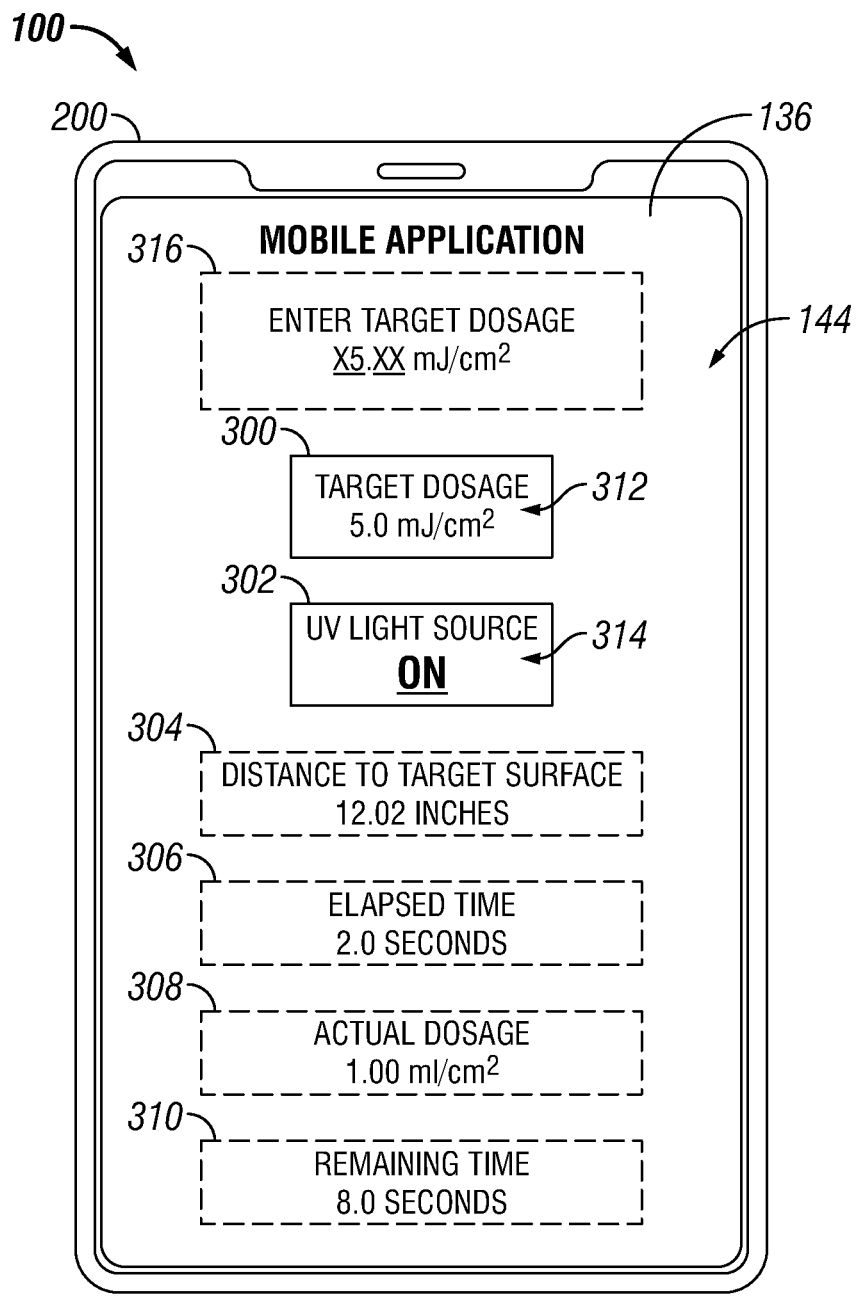
FIG. 3A illustrates a front view of a user interface of the portable communication device of FIG. 2, in accordance with one or more embodiments of the disclosure.

FIG. 3A illustrates a front view of the user interface 136 of the mobile device 200 of FIG. 2, in accordance with one or more embodiments of the disclosure. Moreover, the mobile device 200 may include the mobile app 144 installed on the mobile device 200. The user may access the mobile app 144 via the user interface 136 of the mobile device 200 (e.g., touchscreen, keypad, etc.). The mobile app 144 may include options to control operation of the UV light source 102 (e.g., shown in FIG. 2), view operation data corresponding to the UV disinfection system 100, output the operation data, etc. In some embodiments, the mobile app 144 is configured to display real-time operation data corresponding to the UV disinfection system 100. For example, the mobile app 144 may include the user interface 136 showing a first display frame 300 for a selected target dosage, a second display frame 302 for an activation status of the UV light source (e.g., on/off), a third display frame 304 for the distance 108 of the mobile device 200 to target location 106 (e.g., shown in FIG. 2), a fourth display frame 306 a timer with elapsed time from UV light source 102 activation, a fifth display frame 308 for an actual dosage estimation, a sixth display frame 310 for an estimated dynamic countdown clock for target dosage, and/or other frames for cumulative use tracking or any other suitable metric for the UV disinfection system 100.

In one example, the user may open the mobile app 144 to view the user interface 136, which may show a user interface target dosage button (e.g., target dosage button 312) proximate a user interface UV light source activation button (e.g., UV activation button 314). The user may select the target dosage button 312 to open an option window 316 for adjusting the target dosage. Alternatively, the target dosage may be fixed, and the mobile app 144 may be configured to automatically deactivate the UV light source 102 (e.g., shown in FIG. 2) upon reaching the target dosage. Moreover, the user may select the UV activation button 314 to activate/deactivate the UV light source 102. Upon activation of the UV light source 102, display frames set forth above 304, 306, 308, and 310 may appear proximate the UV activation button 314 to show the distance 108 of the mobile device 200 from the target location 106, the actual dosage, the timer with elapsed time from the UV light source 102 activation, the estimated dynamic countdown clock for the target dosage, or some combination thereof. In some embodiments, moving the mobile device 200 (i.e., changing the distance 108 between the mobile device 200 and the target location 106) may cause the countdown clock for the target dosage to update in real-time. For example, moving the mobile device 200 away from to the target location 106 may increase the duration of the countdown clock. The mobile app 144 may include any suitable user interface features for controlling operation of the UV light source 102, viewing operation data corresponding to the UV disinfection system 100, and/or outputting the operation data.

In some embodiment, the mobile app 144 includes processor executable instructions configured to activate various components before, during, or after activation or deactivation of the UV light source 102, or some combination thereof. For example, the mobile app 144 may be configured to activate the speaker device 146 (e.g., show in FIG. 2) in response to deactivation of the UV light source. In another example, the mobile app 144 may be configured to activate the visible light source 126 (e.g., shown in FIG. 2) in response to activation of the UV light source 102. Moreover, the mobile app 144 may include processor executable instructions configured to receive the tilt angle signal from the mobile device 200 and to generate a deactivation signal for deactivating the UV light source 102 in response to a maximum tilt angle having been exceeded. For example, the mobile app 144 may generate the deactivation signal in response to the tilt angle exceeding −45 degrees (e.g., maximum tilt angle) with respect to a horizontal plane. That is, a range of operation for the UV light source may be between −90 degrees (e.g., downward) to −45 degrees.

Figure 3B:
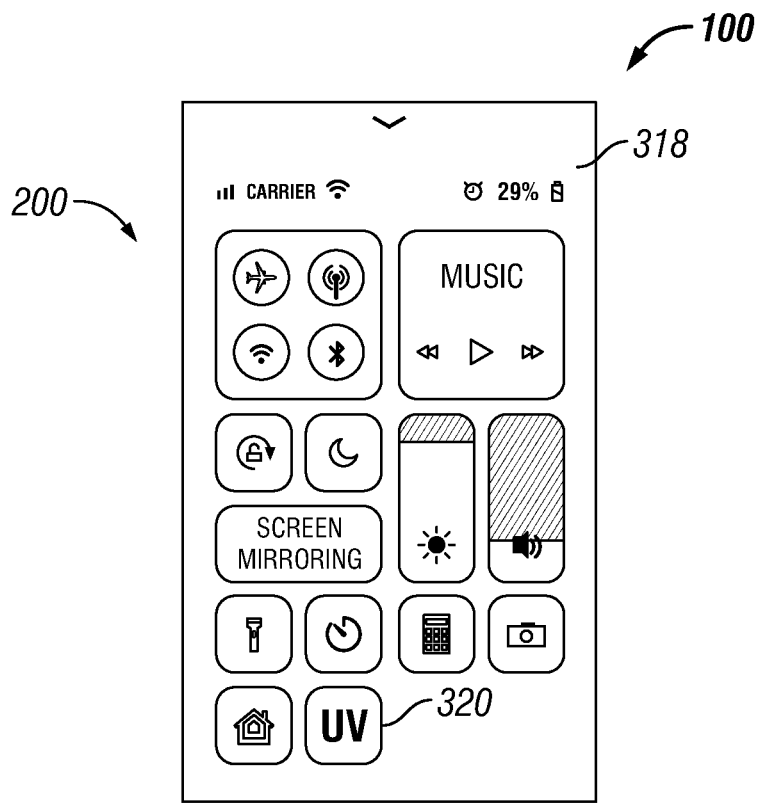
FIG. 3B illustrates a front view of another user interface for a portable communication device of FIG. 2, in accordance with one or more embodiments of the disclosure.

FIG. 3B illustrates a front view of another user interface 318 for another embodiment of the mobile device 200 of FIG. 2, in accordance with one or more embodiments of the disclosure. The mobile device 200 is loaded with an application (e.g., mobile app 144). In this embodiment, the user points the mobile device 200 at the target location 106 (e.g., shown in FIG. 2) and depresses an icon 320. The icon 320 may be generated based at least in part on computer executable instructions to provide an interface to allow the user to provide user input. Moreover, in response to the user depressing the icon 320, the system may calibrate based on the distance 108 (e.g., shown in FIG. 2) using the rear camera 204 (e.g., shown in FIG. 2) or the distance measuring device. Upon calibration, the UV disinfection system 100 activates the UV light source 102 (e.g., shown in FIG. 2) and the visible light source 126 (e.g., shown in FIG. 2) for the "disinfection mode." Once the dosimetry circuit 112 senses that target dose has been emitted to the target location, the UV disinfection system 100 automatically deactivates. If any sensor is disturbed, the UV light source 102 shuts down automatically and an error code is given.

Figure 3C:
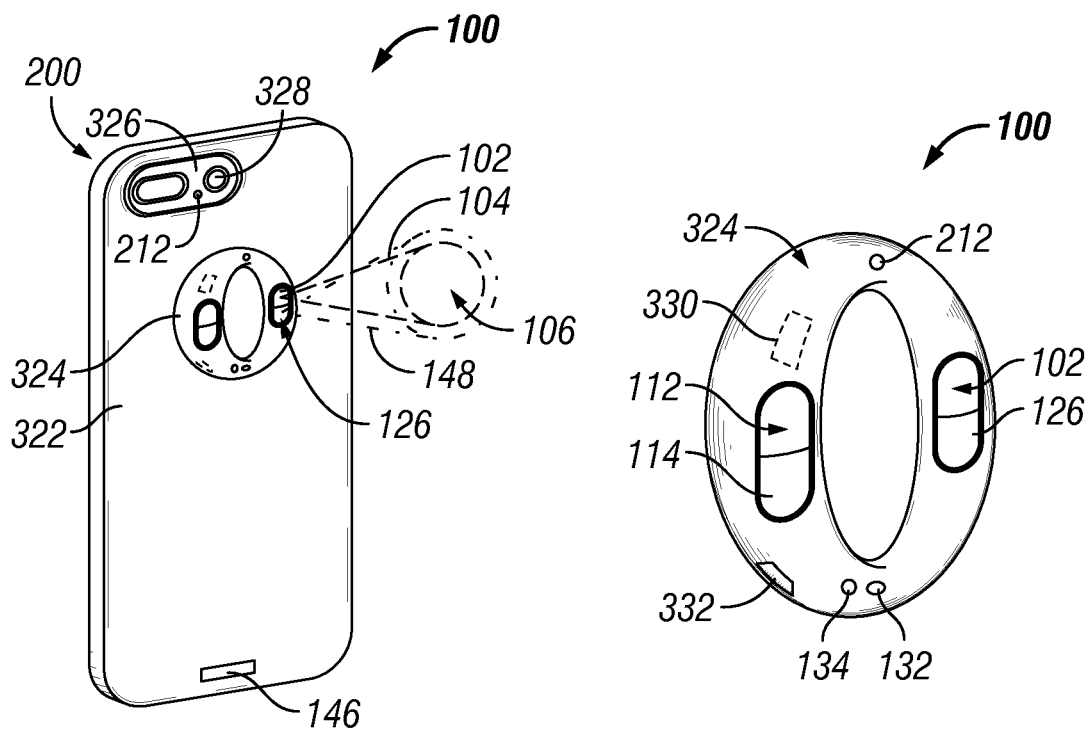
FIG. 3C illustrates a portable communication device with a cover that incorporates the UV disinfection system, in accordance with one or more embodiments of the disclosure.

FIG. 3C illustrates the mobile device 200 with a cover 322. In the illustrated embodiment, the cover 322 is configured to protect an exterior housing 326 of the mobile device 200. A UV disinfection apparatus 324 (e.g., cover element) may be configured to mount (e.g., snap) onto the cover 322. In some embodiments, the UV disinfection apparatus 324 may be configured to mount directly onto the exterior housing 326 of the mobile device 200. Indeed, the UV disinfection apparatus 324 may be an accessory for the mobile device 200. Further, as in the embodiment of FIG. 3B, the mobile device 200 may be loaded with an application (e.g., mobile app 144 shown in FIG. 1) configured to interact with the UV disinfection apparatus 324. For example, the UV disinfection apparatus 324 may include a Bluetooth transceiver for transmitting and/or receiving data or command signals to/from the application.

Moreover, the UV disinfection apparatus 324 (e.g., cover element) incorporates the UV disinfection system 100. Accordingly, the UV disinfection apparatus 324 includes the UV light source 102 configured to emit the UV light 104 having a mean peak wavelength between 200-280 nanometers toward the target location 106 to at least partially inactivate pathogens exposed to the emitted UV light 104 in the path of the emitted UV light 104 and a surface of the target location 106. The UV disinfection apparatus 324 may also include the visible light source 126 configured to emit visible light 148, which may provide an indication that the UV light source 102 is active.

The UV disinfection apparatus 324 may also include the UV sensor 114, or other distance measuring system, configured to determine a distance between the UV light source 102c and the target location 106. For example, the UV sensor 114 may determine the distance from the target location 106 based upon sensing the UV light 104 reflected from the target location 106. Based on the determined distance between the UV light source 102 and the target location 106, the UV sensor 114 or other distance measuring system may generate a distance input signal. The UV disinfection apparatus 324 may also include the dosimetry circuit 112 or algorithm configured to receive the distance input signal and generate a cumulative dose signal indicating a cumulative dose of UV light received at the target location 106 in real-time based at least upon the distance input signal and an intensity of the UV light 104 emitted from the UV light source 102. The application may include processor executable instructions configured to receive the cumulative dose signal and to send a deactivation signal to the UV light source 102 when the cumulative dose signal indicates that a target dose has been achieved. Moreover, the UV disinfection apparatus 324 may also include the temperature sensor (e.g., IR sensor 132) or the motion sensor 134 configured to provide a deactivation input signal to the application upon sensing a particular temperature or motion within the UV light 104 emitted from the UV light source 102.

In one example, a user points the UV disinfection apparatus 324 at the target location 106 and depresses the icon 320 (e.g., shown in FIG. 3B). In response to depressing the icon 320, the application calibrates the UV disinfection system 100 based on the UV sensor 114 or other distance measuring system. Upon calibration, the UV disinfection system 100 activates the UV light source 102 and the visible light source 126 for the "disinfection mode." The visible light source 126 may be of a wavelength and color that are different and readily distinguishable to the user from the wavelength and color of a flashlight 328 of mobile device 200. Once the dosimetry circuit 112 senses that the target dose has been achieved (e.g., emitted to the target location 106), the UV disinfection system 100 may automatically deactivate. If any sensor is disturbed, the UV light source 102 shuts down automatically and an error code is given. In some embodiments, the user may reset the UV disinfection apparatus 324 in response to deactivation.

The UV disinfection apparatus 324 may include other components such as the tilt sensor 212 to provide a tilt angle signal indicating a tilt angle of the mobile device 200. The application may include processor executable instructions configured to monitor the tilt angle signal and generate a deactivation signal for communication to the UV light source 102 to deactivate the UV light source 102 in response to a maximum tile angle having been exceeded. Alternatively, the mobile device 200 may include the tilt sensor 212. Accordingly, the application may include processor executable instructions configured to receive the tilt angle signal from the mobile device 200 and to generate a deactivation signal for deactivating the UV light source 102 in response to a maximum tilt angle having been exceeded. Further, the UV disinfection apparatus 324 may include its own power and charging system including an internal battery 330, USB charging/data transfer port 332, or wireless charging capability so that it may be charged by adjacent mobile device 200 or adjacent wireless charging source, or via a hardwire connection to a standard USB charging port of mobile device 200.

Moreover, the mobile device 200 may include components such as the speaker device 146. The application may include processor executable instructions configured to activate the speaker device 146 to emit an audible sound before, during, or after activation or deactivation of the UV light source 102, or some combination thereof.

Figure 4:
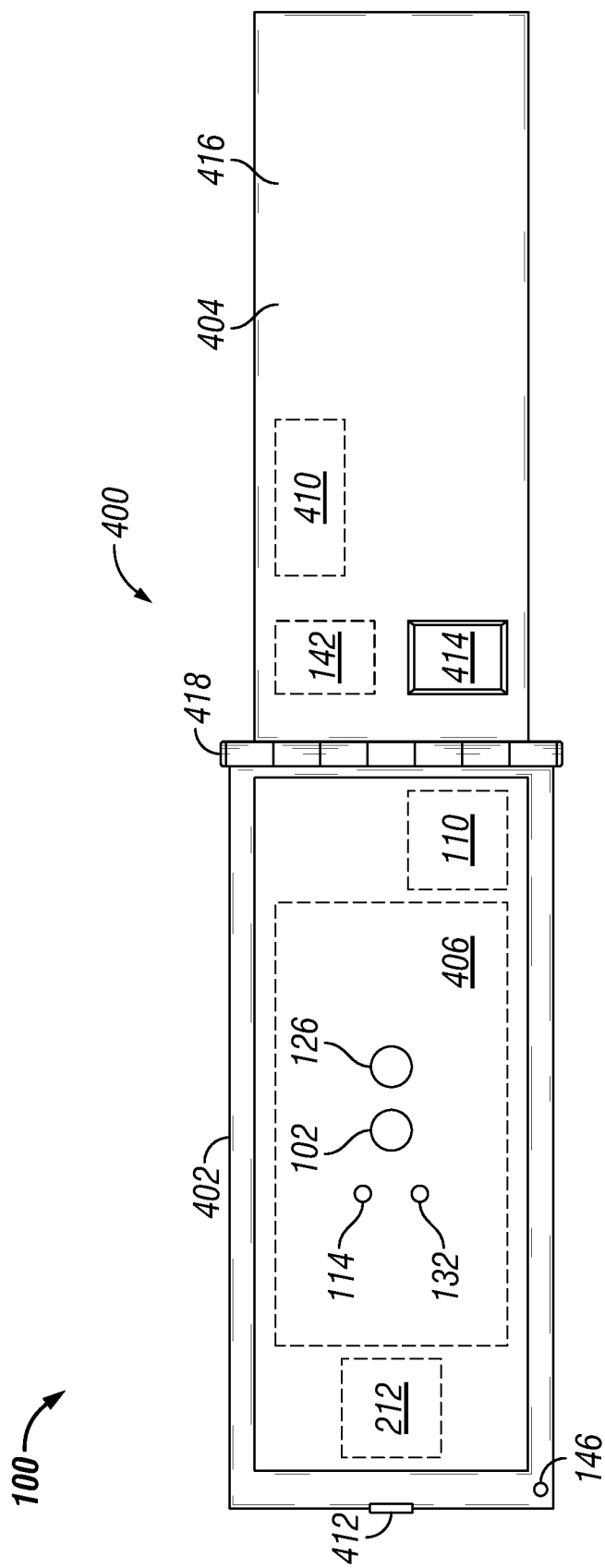
FIG. 4 illustrates a perspective view the UV disinfection system including a portable device, in accordance with one or more embodiments of the disclosure.

FIG. 4 illustrates a perspective view the UV disinfection system 100 including a portable handheld device 400, in accordance with one or more embodiments of the disclosure. Similar to the UV disinfection system 100 for the mobile device 200 of FIG. 2, the portable UV disinfection system 100 may include the UV light source 102 configured to emit UV light 104 to at least partially inactivate a pathogen at the target location 106 (e.g. shown in FIG. 1), as well as the visible light source 126 configured to emit visible light indicating that the UV light source 102 is active. As illustrated, the UV light source 102 and the visible light source 126 of the UV disinfection system 100 are secured to the portable handheld device 400. The portable handheld device 400 includes a housing 402 with a handle portion 404 and a display portion 406. The UV light source 102 and the visible light source 126 may be secured to a portion of the portable handheld device opposite the display portion 406, such that a user may view the display portion 406 while directing the UV light beam 104 and/or the visible light beam 148 away from the user. The user may hold portable handheld device 400 during operation (e.g., while directing the UV light beam 104) without being directly exposed, or exposing others to the emitted UV light 104.

The portable UV disinfection system 100 may also include a tilt sensor 212 disposed within the housing 402 of the portable handheld device 400. The tilt sensor 212 is configured to detect a tilt orientation of the portable handheld device 400 with respect to a horizontal plane (e.g., the ground). For example, a zero degree orientation may indicate that the portable handheld device 400 is oriented such that the UV light beam 104 is directed horizontally or in parallel to the ground, whereas a negative ninety degree angle may indicate that the UV light beam 104 is directed downward to the ground. In the context of the aforementioned coordinate system, the UV disinfection system 100 may be configured to automatically shut down the UV light source 102 in response to detecting that the tilt orientation of the portable handheld device 400 is, for example between −45 and +90 degrees relative to the horizontal plane. In some embodiments, the mobile application 144 may allow the user to disable the tilt orientation auto-shut down feature such that the user may operate the portable handheld device at the tilt orientation less than a pre-determined angle, for the purposes of the example above, of −45 degrees.

Further, the portable UV disinfection system 100 may include the infrared sensor 132 and/or the UV sensor 114 as set forth above in FIG. 2. The infrared sensor 132 and/or the UV sensor 114 may be secured to the portable handheld device 400 proximate the UV light source 102. That is, the infrared sensor 132 and/or the UV sensor 114 may be secured to the portion of the portable handheld device 400 opposite the display portion 406. The infrared sensor 132 and/or the UV sensor 114 may be configured to output data (e.g., temperature data, UV light reflection data, etc.) to the controller 110 of the portable UV disinfection system 100 disposed within the housing. The controller 110 may be configured to activate, shut-down, or adjust a power of the UV light source 102 based at least in part on the data outputs from the infrared sensor 132 and/or the UV sensor 114. In some embodiments, the controller 110 is configured to output the data to the mobile app 144 (e.g., shown in FIG. 3) for display on the display portion 406 of the portable handheld device 400. The display portion 406 of the portable handheld device 400 may include a color display. The display portion 406 may also comprise a touchscreen display configured to receive input from the user. Moreover, in some embodiments, the controller 110 is configured to output signals to the speaker device 146 secured to the housing 402 of the portable handheld device 400. The signals may be configured to cause the speaker device 146 to output chimes and/or other alerts based at least in part on a status of the UV disinfection system 100. For example, the speaker device 146 may output a chime, tone, song, or other suitable sound, indicating activation and/or operation of the UV light source 102.

Moreover, the portable UV disinfection system 100 may also include communications circuitry 142 (e.g., a Bluetooth circuit, or any other suitable wireless protocol) for providing wireless functionality to the UV disinfection system 100. The wireless functionality may allow the user to track user-specific operational data via the mobile app 144. The wireless functionality may also facilitate data upload to a cloud server and/or permit downloads for firmware updates. In some embodiments, the user may remotely access the operational data for the portable UV disinfection system 100 by accessing the mobile app 144 from an internet enabled device such as a mobile phone, tablet, desktop computer, or any other suitable device.

The UV disinfection system 100 may include other components secured to the housing of the portable handheld device 400. For example, the UV disinfection system 100 may include a battery 410 for powering the device, a USB charging port 412 for recharging the battery and/or data transfer, a power button 414 for activating the portable handheld device, a flip cover 416 for protecting the screen when the device is not in use, an integrated hinge 418 for facilitating movement of the flip cover 416, and/or any other suitable component.

Figure 5:
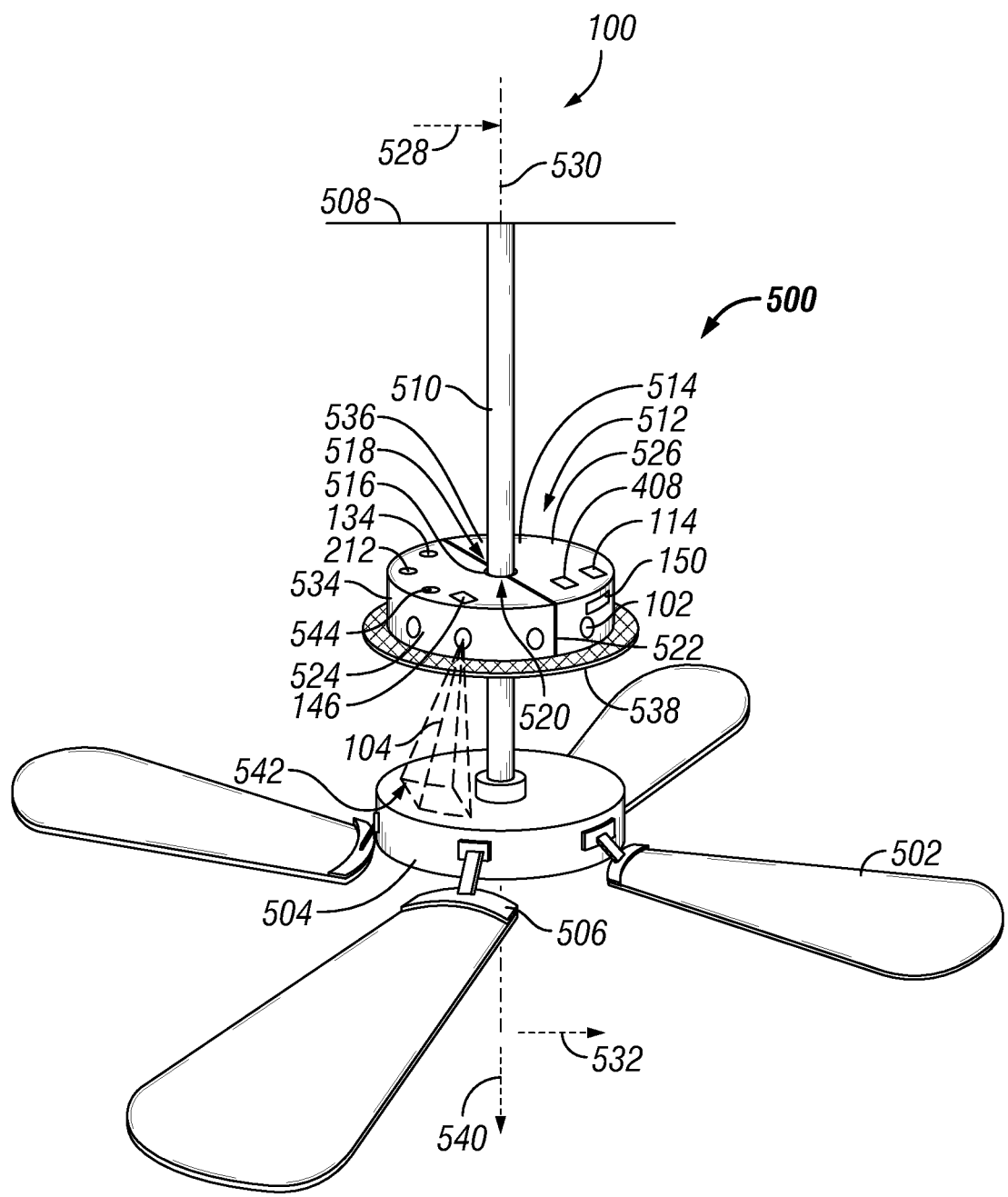
FIG. 5 illustrates a perspective view of the UV disinfection system on a fan, in accordance with one or more embodiments of the disclosure.

FIG. 5 illustrates a perspective view of the UV disinfection system 100 on a fan 500, in accordance with one or more embodiments of the disclosure. In the illustrated embodiment, the fan 500 includes a ceiling fan 500. However, the fan 500 may include any rotary device configured to circulate air. As illustrated, the ceiling fan 500 includes a plurality of fan blades 502 secured to a fan motor housing 504 via corresponding fan blade holders 506. A motor is disposed in the fan motor housing 504 and is configured to drive rotation of the fan blades 502 with respect to the fan motor housing 504 to drive air (e.g., induce airflow) in a direction transverse to rotation of the fan blades 502 (e.g., upwards or downwards). The motor may be configured to rotate the fan in either a first or a second rotational direction opposite to the first rotational direction. The fan motor housing 504 may be secured to a ceiling 508 of an interior room of a dwelling via a downrod 510. A UV disinfection assembly 512 of the UV disinfection system 100 may be secured to the downrod 510 of the fan 500. In particular, the UV disinfection assembly may include a housing 514 secured to the downrod 510 via at least one fastening feature 516.

The housing 514 may have a cylindrical shape with an axial bore 518 extending through a central portion 520 of the housing 514. However, the housing 514 may include any suitable shape. A diameter of the axial bore may be sized such that the downrod 510 may be inserted into the axial bore. In one example, the fastening feature 516 includes compression clamps configured to secure the housing 514 to the downrod 510 once the housing 514 is disposed around the downrod 510. During installation, the housing 514 may slide over the downrod 510 to a desired position with respect to the fan motor housing 504. Once in position, the compression clamps may be actuated to secure the housing 514 in position. In some embodiments, the housing 514 may be a split housing 514 with a hinge 522 connecting a first portion 524 and a second portion 526 of the housing 514. The split housing 514 may be configured to open via the hinge 522, slide over the downrod 510 in a direction 528 transverse to the axis 530 of the downrod 510, and then close to clamp around the downrod 510. The split housing 514 may provide for ease of installation as the housing 514 may be installed to existing fans 500 without having to detach the downrod 510 from the fan motor housing 504 or the ceiling. In some embodiments, the UV disinfection system 100 includes the tilt sensor 212 and/or a motion sensor 134 configured to prevent operation of the UV disinfection system 100 unless the housing 514 is in a proper orientation with respect to the fan 500. The UV disinfection system 100 may also include other components such as the sensor 544, the UV sensor 114, the speaker device 146, air freshener 150, the tilt sensor 212, etc.

Moreover, in the illustrated embodiment, the UV disinfection system 100 includes a plurality of UV light sources 102 configured to emit UV light 104 into a path of the air driven (e.g., pulled or pushed) by the fan 500 to at least partially inactivate pathogens in the air proximate the fan 500. In particular, the plurality of UV light sources 102 configured to emit UV light 104 in a substantially horizontal path substantially normal to the direction of the induced airflow. In the illustrated embodiment, the plurality of UV light sources 102 is configured to emit the UV light 104 in a direction 532 radially outward from the downrod 510. Accordingly, the plurality of UV light sources 102 may be disposed around a radially outer surface 534 of the housing 514. However, in some embodiments, the UV disinfection system 100 may include at least some of the UV light sources 102 (e.g., UV LEDs or UV bulbs) disposed on other surfaces (e.g., a top surface 536 or a bottom surface) of the housing 514. While active, each of the plurality of UV light sources 102 emit UV light 104 at a mean peak wavelength between 200-280 nanometers. Alternatively, the mean peak wavelength range may be between 200-250 nanometers, 200-220 nanometers, or any other suitable range. Moreover, to inactivate the pathogens in the air proximate the fan 500 at a desired rate, each UV light source 102 may be configured to emit the UV light 104 at a power of 0.1-150 watts into a respective target volume 542 corresponding to the UV light source 102. In some embodiments, the UV disinfection system 100 may include a switch configured to activate the UV light source in response to activation of the motor.

In some embodiments, the UV disinfection system 100 may include a baffle plate 538 configured to control a beam angle of the UV light 104 emitted from each of the plurality of UV light sources 102. In the illustrated embodiments, the baffle plate 538 may restrain the UV light beams 104 from emanating in a vertically downward direction 540 toward an area beneath the fan 500 such that UV disinfection system 100 may operate without any direct exposure to people congregated in the area beneath the fan 500. As such, the baffle plate 538 may be disposed between the UV light sources 102 and the fan motor housing 504. Although the baffle plate 538 is configured to constrain the UV light beams 104, the baffle plate 538 may be positioned and sized to minimize interference of the baffle plate to the flow of air caused by operation of the fan 500. In some embodiments, an outer diameter of the baffle plate 538 is less than or equal to a diameter of the fan motor housing 504. However, the baffle plate has a larger diameter than an outer diameter of the housing 514 of the UV disinfection system 100 such that the baffle plate 538 may restrain the UV light beams 104.

In some embodiments, the UV disinfection system 100 may include a sensor 544 (e.g., a temperature or motion sensor) configured to detect a temperature or a motion in a volume below the fan 500 and to provide an activation input signal to activate the UV light source 102 in response to sensing a particular temperature or motion in the volume below the fan 500. For example, the sensor 544 may be configured to provide the activation signal in response to detecting a temperature below the fan 500 corresponding to a human being such that the UV light source 102 activates when a person is in the volume (e.g., room, space, etc.) below the fan 500.

In some embodiments, the UV disinfection system 100 may include components for time-based control and monitoring of the UV disinfection system 100. For example, the UV disinfection system 100 may include a clock circuit, a signal generator configured to generate a time signal indicating the times when the UV light source is active, a transmitter configured to transmit the time signal, and a recording device configured to receive the time signal and record the times during which the UV light source 102 is active. The recording device may include a software application with processor executable instructions configured to record the times during which the UV light source is active, as well as operate the fan 500 and/or the UV light source 102. In some embodiments, the recorded times may be output to the controller 110 (e.g., shown in FIG. 1). Moreover, controller 110 may be configured to output executable instructions to activate the fan 500 and/or the UV light source 102 at pre-set times.

Figure 6:
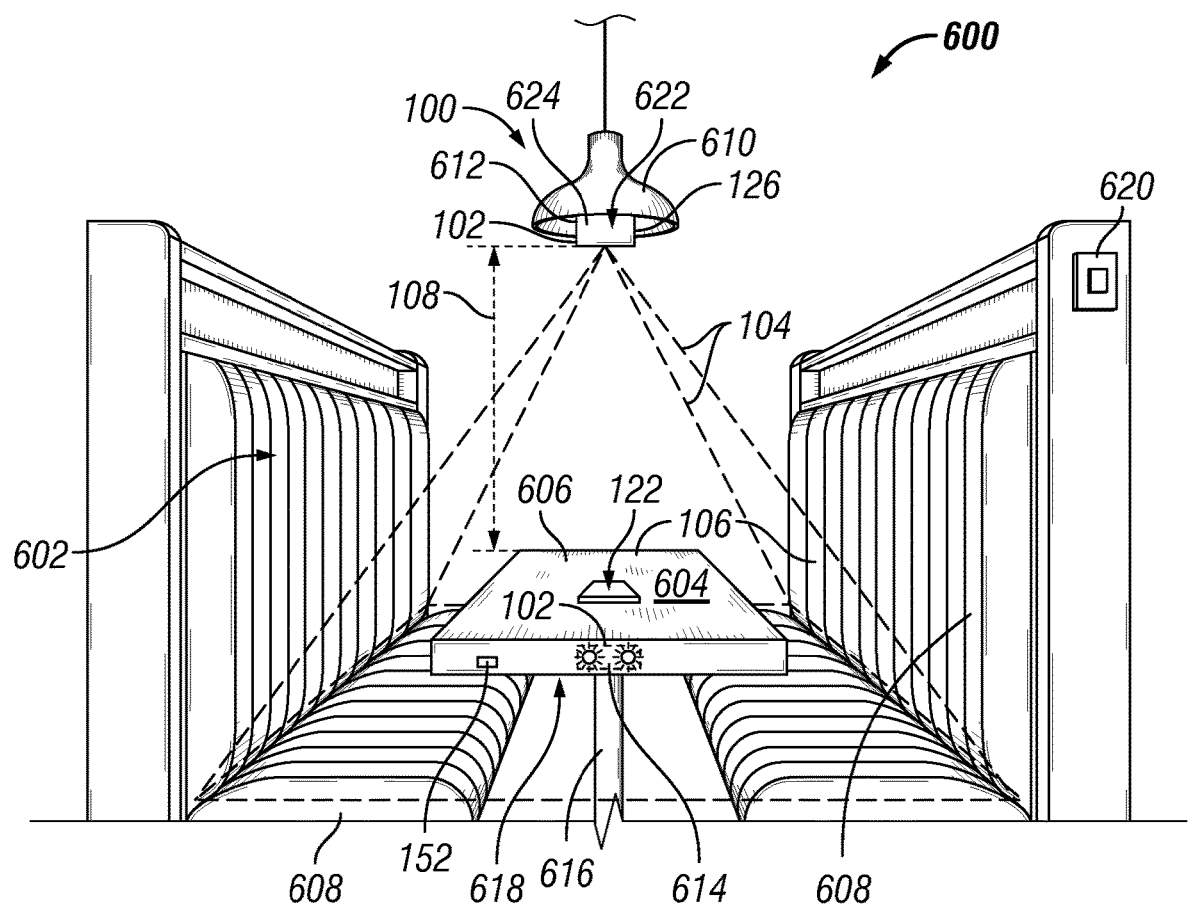
FIG. 6 illustrates a perspective view of the UV disinfection system in an indoor public space such as a restaurant, in accordance with one or more embodiments of the disclosure.

FIG. 6 illustrates a perspective view of the UV disinfection system 100 in an indoor public space such as a restaurant 600, in accordance with one or more embodiments of the disclosure. In other examples, the UV disinfection system 100 may be disposed at a counter in a bar, in a public transportation vehicle such as a bus, train, or subway, at a conference room table, or within any other suitable indoor public indoor space. In the illustrated embodiment, seating arrangements 602 at restaurants are generally used by multiple parties of people throughout a day, some of which may be carriers of a pathogen (e.g., Covid-19). In between parties, a busser generally clears and wipes down a restaurant table 604 at the seating arrangement 602. However, pathogens may still remain on the surface 606 of the restaurant table 604 and/or other surfaces (e.g., chairs, benches 608, arm rests, etc.) of the seating arrangement 602. To minimize risk a pathogen transmission via contamination of the seating arrangement 602, the UV disinfection system 100 is configured to at least partially inactivate pathogens that may be present on these surfaces (e.g., target locations 106). Specifically, to at least partially inactivate the pathogens, the UV disinfection system 100 includes at least one UV light source 102 configured to emit UV light at a mean peak wavelength between 200-280 nanometers toward the target locations 106 (e.g., the restaurant table 604, the benches 608, etc.) of the seating arrangement 602. Alternatively, the mean peak wavelength range may be between 200-250 nanometers, 200-220 nanometers, or any other suitable range.

The at least one UV light source 102 may be configured to activate when a corresponding seating arrangement 602 is unoccupied. For example, after a party leaves the seating arrangement 602 and a busser clears the restaurant table 604, the UV light source 102 may automatically activate for a disinfecting cycle. In another example, the busser may actuate a switch 620 to activate the disinfecting cycle, by direct action or via remote communication such as Bluetooth, or any suitable wireless protocol. The UV light source 102 is configured to provide a target dosage of UV light 104 to the target locations 106 at the seating arrangement 602 during the disinfecting cycle. For example, the target dosage may be 1-100 millijoules/cm$^2$. The UV disinfection system 100 may be configured to adjust various parameters (e.g., power, duration, etc.) for the UV light source 102 based on a position of the UV light source 102 to achieve the target dosage. For example, a first UV light source 102 disposed proximate a light fixture 610 of the seating arrangement 602 may be between 3-10 feet from the target location 106 (e.g., the restaurant table 604. Based at least in part on the distance 108 of the UV light source 102 from the target location 106, the UV light source 102 may be configured to emit UV light 104 with a power draw of 0.1-150 watts for 10 to 120 seconds to achieve the target dosage. Providing the target dosage to the target location 106 may at least partially inactivate pathogens (e.g., Covid-19), thereby, reducing a risk of pathogen transmission to subsequent patrons entering the seating arrangement 602.

Further, to provide the target dosage to each of the surfaces 604, 608 of the seating arrangement 602, the UV disinfection system 100 may include a plurality of UV light sources 102. In the illustrated embodiment, the UV disinfection system 100 includes a first UV light source 612 disposed above the seating arrangement 602. Specifically, the first UV light source 102 is disposed proximate the light fixture 610 positioned above the restaurant table 604 and may be configured to emit UV light 104 in a downward direction toward the restaurant table 604 and the benches 608. Additionally, the UV disinfection system 100 includes a second UV light source 614 disposed below the restaurant table 604 to disinfect surfaces at the seating arrangement 602 that are not in line of sight of the first UV light source 102. The second UV light source 614 may be secured to a center post 616 of the restaurant table 604 such that the second UV light source 614 may emit UV light 104 radially outward to a bottom surface 618 of the restaurant table 604, as well as to other surfaces that are not exposed to the UV light 104 from the first UV light source 102. In another embodiment, the UV disinfection system 100 may include additional UV light sources 102 that may be disposed in any suitable positions proximate the seating arrangement 602. Further, the UV disinfection system 100 may include aprons, baffles, etc. to control beam angles for the UV light 104 emitted from the respective UV light sources 102.

Moreover, the UV disinfection system 100 may also include at least one UV detector 122 positioned on the target locations 106 (e.g., the restaurant table 604, the benches 608, etc.) of the seating arrangement 602. The UV detector 122 may be embedded in or secured to the target location 106 via coatings, surface materials, adhesives, clamps, or other suitable fasteners. As set forth above, the UV detector 122 is configured to provide an indication of an amount of exposure of the target location 106 to the UV light 104 emitted from the UV light sources 102. Each UV detector 122 is configured to changes colors in response to exposure to UV light 104 having the mean peak wavelength between 200-280 nanometers. The UV detector 122 may include a photochromic pigment, dye, or other colorants that have the property of changing color under the UV light having a mean peak wavelength between 200-280 nanometers. In some embodiments, the UV detector 122 is configured to gradually change colors based at least in part on a dosage of UV light 104. For example, once 10 percent of the target dosage has been delivered, the UV detector 122 may have a red color. At 50 percent of the target dosage (e.g., a midpoint to the target dosage), the UV detector 122 may have a yellow color. Further, at completion of the target dosage, the UV detector 122 may have a green color to indicate that the target location 106 has been exposed to the target dosage. In some embodiments, the UV detector 122 is configured to revert from the green color back to the red color over time. For example, the UV detector 122 may revert from green to red over a period of 10-600 seconds. In another example, after UV light source 102 deactivate and exposure to the UV light 104 ceases, the UV detector 122 may revert from green to red over a period of 2-10 minutes.

In some embodiments, the UV disinfection system 100 includes a light array 622. The light array may include a frame 624 configured to house a plurality of UV light sources 102 and a plurality of visible light sources 126. As set forth above, each UV light source 102 is configured to emit ultraviolet light having a mean peak wavelength between 200-280 nanometer to at least partially inactivate pathogens exposed to the emitted UV light 104. Moreover, each of the UV light sources 102 and the visible light sources 126 are configured to produce an individual light beam having an individual volume between the individual sources and a corresponding target location 106 (e.g., a surface area located at a given distance away from the individual source). The UV light sources 102 and the visible light sources 126 may be individually adjusted to point towards corresponding target locations 106.

Moreover, the plurality of UV light sources 102 of the light array 622 are collectively configured to produce a collective UV light beam having a collective volume between the light array 622 and a collective target surface area. The collective target area may include the table 604, the seating arrangement 602, an area where people may congregate, or some combination thereof. In another example, the collective target area may include a keypad, touchscreen, or any surface disposed in a public space. Further, the plurality of visible light sources 126 are configured to collectively illuminate the collective target area to indicate that the UV light sources 102 are active and the UV disinfection system 100 is in a disinfection mode. The controller 110 (e.g., shown in FIG. 1) is configured to send a first signal to the light array 622 to activate the light array 622 (e.g., the UV light sources 102 and the visible light sources 126) and a second signal to the light array 622 to deactivate the light array 622. In some embodiments, the controller 110 includes a deactivation circuit or algorithm to deactivate the light array 622 when the deactivation circuit or algorithm determines that the target dosage of UV light 104 has been achieved at the collective target surface area. The deactivation circuit or algorithm may determine that a target dosage of UV light 104 has been achieved on the collective target surface area based upon at least in part on an intensity of the UV light 104 and the distance between each UV light source and its corresponding target surface area. In some embodiments, the deactivation circuit or algorithm may determine that a target dosage of UV light 104 has been achieved when the determined target dosage is 1-120 millijoules/cm2 at the target location 106.

The UV disinfection system 100 may also include a proximity sensor 152 configured to detect the presence of a human being within a given safety volume greater than or equal to the target volume and to emit a motion signal to the controller 110 to deactivate the light array 622 upon detecting the presence of a human being in the given safety volume. In some embodiments, the proximity sensor 1152 is a temperature sensor configured to monitor a temperature in a predetermined range within the target volume. The predetermined range may be between 95-105 degrees Fahrenheit or over 10 degrees Fahrenheit above ambient or room temperature within the target volume. In some embodiments, the proximity sensor 152 is a motion sensor configured to detect when an object or human being has moved into the UV light path within the target volume.

Figure 7:
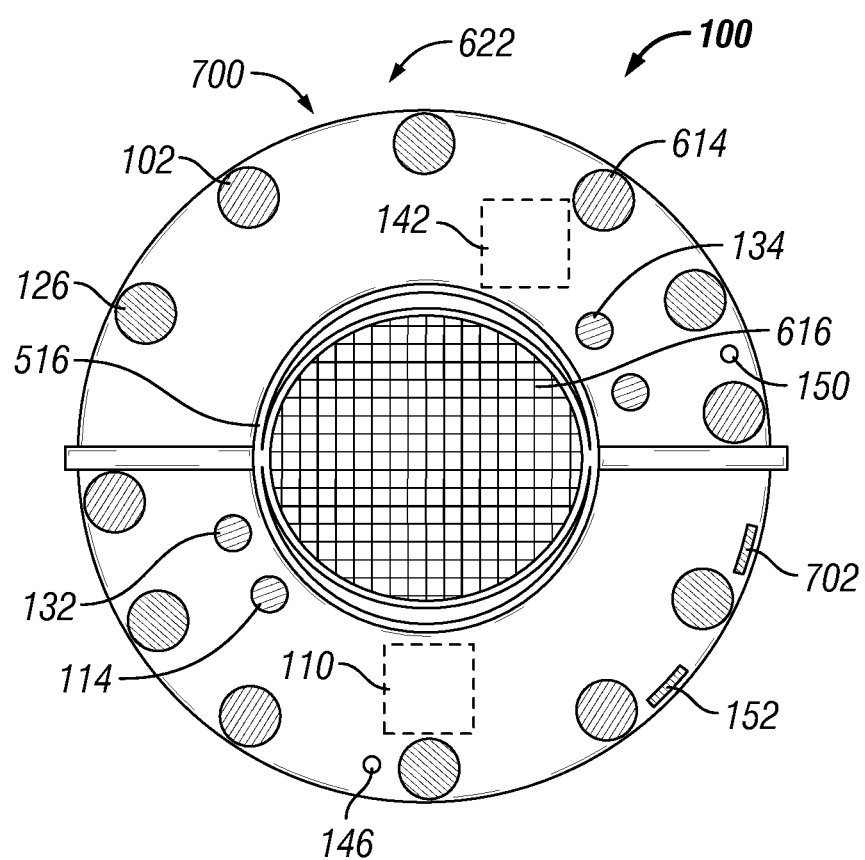
FIG. 7 illustrates a bottom view of a table mounting assembly for housing the second UV light source of FIG. 6, in accordance with one or more embodiments of the disclosure.

FIG. 7 illustrates a bottom view of a table mounting assembly 700 for housing the second UV light source 614 of FIG. 6, in accordance with one or more embodiments of the disclosure. As set forth above, the UV disinfection system 100 may include the first UV light source 612 and the second UV light source 614, as well as corresponding visible light sources 126. The light sources 102, 126 may be housed within the corresponding UV disinfection assemblies (e.g., light arrays 622). For example, in the illustrated embodiment, UV disinfection system 100 includes the table mounting assembly 700 for housing the second UV light source 614 and the visible light source 126. The table mounting assembly 700 may be configured to attach to an underside of the restaurant table 604 (e.g., shown in FIG. 6). Specifically, the table mounting assembly 700 may be configured to attach to the center post 616 of the restaurant table 604. The table mounting assembly 700 may include at least one fastening feature 516 (e.g., compression fittings) configured to secure the table mounting assembly 700 to the center post 616. However, the table mounting assembly 700 may include any suitable fastening feature 516 for securing the table mounting assembly 700 to the restaurant table 604.

Moreover, the table mounting assembly 700 may be configured to house additional components of the UV disinfection system 100. For example, the table mounting assembly 700 may be configured to house control circuitry (e.g., the controller 110) of the UV disinfection system 100. The control circuitry may be configured to power and/or control operation of the UV light source 102 and the visible light source 126. That is, the control circuitry may activate the UV light source 102 and the visible light source 126 for the disinfection cycle and may deactivate the UV light source 102 and visible light source 126. The control circuitry may be configured to control operation of the UV disinfection system 100 based on manual input from the user interface 136 (e.g., shown in FIG. 1). Alternatively, the control circuitry may automatically control operation of the UV disinfection system 100.

Further, the table mounting assembly 700 may be configured to house a sensor (e.g., infrared sensor 132, UV sensor 114, motion sensor 134, proximity sensor 152, etc.) of the UV disinfection system 100. The sensor may be configured to detect the presence of a person within a vicinity of the seating arrangement 602. For example, the sensor may be the infrared sensor 132 configured to detect a temperature within body temperature range (e.g., 95-105 degrees Fahrenheit) or over 10 degrees Fahrenheit above ambient or room temperature and/or motion proximate the seating arrangement 602. The control circuitry may include an auto-shut feature to deactivate the UV light source 102 (i.e., to switch the UV disinfection system 100 from the disinfection mode to the normal operation mode) if a body temperature or motion are detected. Further, the control circuitry the UV disinfection system 100 may output an alarm code to a user, via communication circuitry (e.g., Bluetooth, WiFi, etc.), in conjunction with deactivating the UV light source 102. That is, the control circuitry may output the alarm code to the mobile app 144 or another suitable location such that the user may receive the alarm code remotely with a device such as a mobile phone, tablet, and desktop computer, etc. Moreover, if the sensor fails to detect a body temperature or motion proximate the seating arrangement 602, the control circuitry may be configured to reactivate the disinfection cycle.

The UV disinfection system 100 may include other features electronically coupled to the control circuitry, which may be housed by the table mounting assembly 700. In some embodiments, the UV disinfection system 100 may include the speaker device 146 configured to produce an audio output to provide audio cues indicating a status of the UV disinfection system 100. For example, the speaker device 146 may be configured to output a first audio cue in response to activation of the disinfection cycle. Further, the speaker device 146 may include other audio cues to indicate that the UV light source 102 is active (i.e., the disinfection cycle is in progress), deactivation of the UV light source 102 due to disinfection cycle completion, deactivation due to auto-shut, or any event related to operation of the UV disinfection system 100. Further, in some embodiments, the UV disinfection system 100 may include a delay switch 702 electronically coupled to the control circuitry. In particular, UV disinfection systems 100 using control circuitry configured to control operation of the UV disinfection system 100 based on manual input from a user may include the delay switch

702. Using manual input systems, the busser or another worker at the restaurant may manually activate the disinfection cycle after clearing the restaurant table 604. The delay switch 702 may be configured to delay activation of the disinfection cycle for at least five seconds from receiving user input to start the disinfection cycle to allow the busser adequate time to move away from the seating arrangement 602 before the disinfection cycle begins. In some embodiments, the UV disinfection system 100 may also include the air freshener 150 configured to output a scented aroma and/or a neutralizing agent in response to activation of the UV light source 102 to provide an indication that the UV light source 102 is active, as set forth above.

Figure 8:
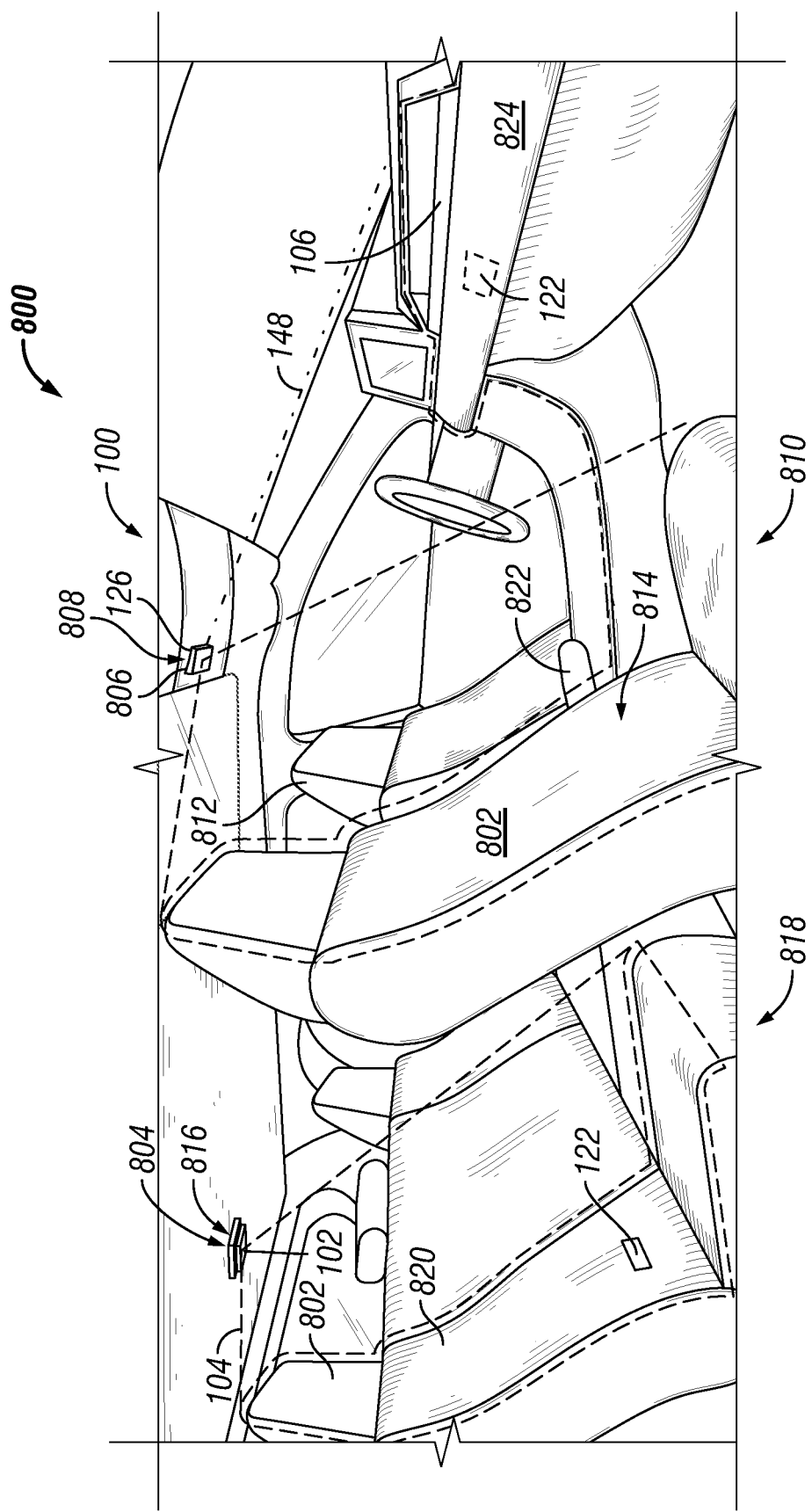
FIG. 8 illustrates a perspective view of the UV disinfection system for disinfecting an interior of a vehicle, in accordance with one or more embodiments of the disclosure.

FIG. 8 illustrates a UV disinfection system 100 for disinfecting an interior of a vehicle 800, in accordance with one or more embodiments of the disclosure. The UV disinfection system 100 is configured to at least partially inactivate pathogens in the exposed air, on passenger seats 802 and/or other surfaces in the vehicle 800. The UV disinfection system 100 includes at least one overhead housing assembly 804 having the UV light source 102 configured to emit UV light 104 at a mean peak wavelength between 200-280 nanometers. Alternatively, the mean peak wavelength range may be between 200-250 nanometers, 200-220 nanometers, or any other suitable range. The UV light source 102 may be secured within the overhead housing assembly 804. Upon activation, the UV light source 102 may be configured to emit UV light 104 through a cover 806, that is at least partially UV-transparent, in a direction toward passenger seats 802 and/or other surfaces of the vehicle 800. In some embodiments, the UV disinfection system 100 may include a plurality of overhead housing assemblies 804. Each overhead housing assembly 804 may be configured to provide UV light 104 to a row of the vehicle corresponding to the overhead housing assembly 804. For example, in the illustrated embodiment, the UV disinfection system 100 includes a first overhead assembly 808 configured to provide UV light 104 to a first row 810 with a driver seat 812 and front passenger seats 814. Further, the UV disinfection system 100 includes a second overhead assembly 816 configured to provide UV light 104 to a second row 818 with rear passenger seats 820. However, any arrangement of overhead housing assemblies 804 may be incorporated in the UV disinfection system 100.

The UV disinfection system 100 may be configured to provide a target dosage of the UV light 104 to the respective target location 106 (e.g., the passenger seats 802 and/or other surfaces of the vehicle) to achieve inactivation of the pathogens on the target location 106. For example, the target dosage may include 1-100 millijoule/cm$^2$ of exposure of the target location 106 to the UV light 104. Moreover, the UV disinfection system 100 may include at least one UV detector 122 positioned on the target location 106. For example, the at least one UV detector 122 may be positioned on the passenger seats 802, a center console 822, a dashboard 824, and/or any other suitable surface for the UV detector 122 within the vehicle 800. In some embodiments, the UV disinfection system 100 may include a plurality of UV detectors 122 positioned within the vehicle 800. The UV detectors 122 may include cards, mats, stickers, etc., positioned on the target location 106. In some embodiments, the target location 106 may include a photochromic material configured to change color in response to exposure to UV light 104. For example, in some embodiments, the seats may include a color changing fabric configured to change color in response to exposure to UV light 104. Each UV detector 122 is configured to provide an indication of exposure of the respective target location 106 to UV light 104. In particular, the UV detector 122 may change colors in response to exposure to the UV light 104 having the mean peak wavelength between 200-280 nanometers. In some embodiments, the UV detector 122 is configured to gradually change colors based at least in part on the actual dosage of UV light 104 provided to the UV detector 122. For example, once 10 percent of the target dosage has been delivered, the UV detector 122 may have a red color. At 50 percent of the target dosage (e.g., a midpoint to the target dosage), the UV detector 122 may have a yellow color. Further, at completion of the target dosage, the UV detector 122 may have a green color to indicate that the target location 106 has been exposed to the target dosage. In some embodiments, the UV detector 122 is configured to revert from the green color back to the red color over time. For example, the UV detector 122 may revert from green to red over a period of 2-10 minutes.

Moreover, the UV disinfection system 100 may include the visible light source 126 secured within the overhead housing assembly 804. The visible light source 126 may be configured to output visible light 148 coincident with the UV light 104 emitted from the UV light source 102.

Figure 9:
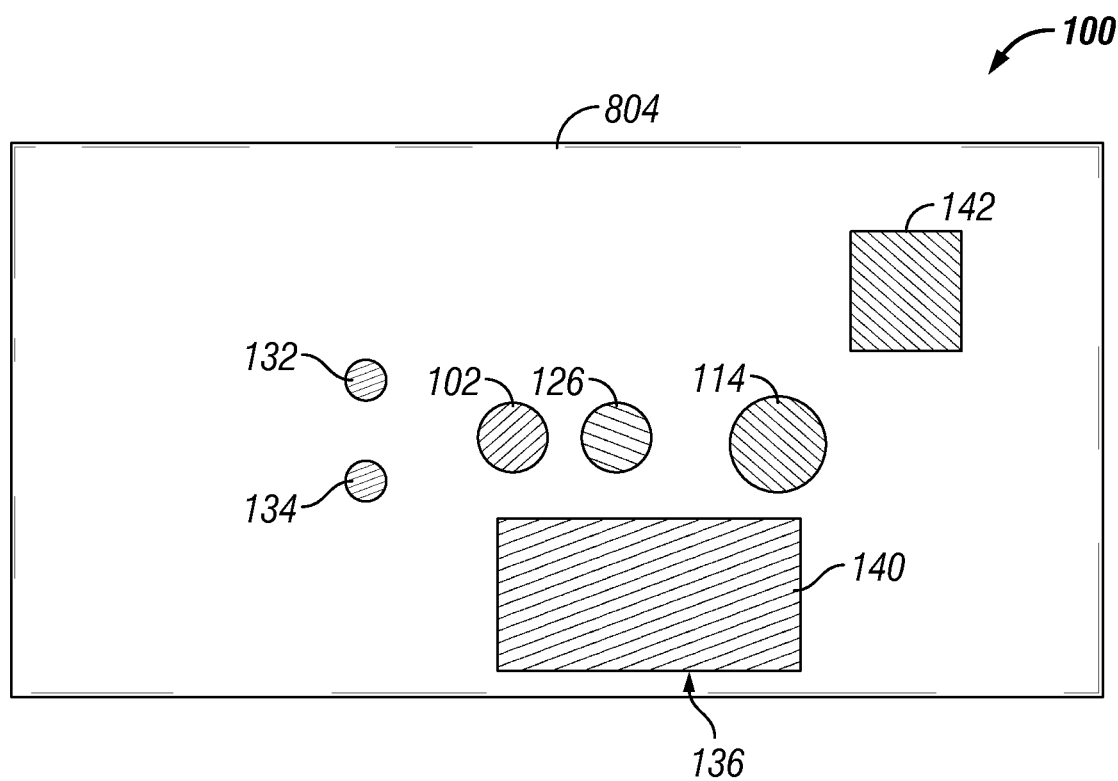
FIG. 9 illustrates a cross-sectional view of the overhead housing assembly of FIG. 8, in accordance with one or more embodiments of the disclosure.

FIG. 9 illustrates a cross-sectional view of the overhead housing assembly 804 of FIG. 8, in accordance with one or more embodiments of the disclosure. As set forth above, the overhead housing assembly 804 includes the UV light source 102 configured to at least partially inactivate pathogens in exposed air, on passenger seats and/or other surfaces in the vehicle. Further, the overhead housing assembly 804 includes the visible light source 126 for providing the visual cues relating to a status of the UV disinfection system 100. However, the overhead housing assembly 804 may include other components configured to provide information related to the status of the UV disinfection system 100.

As illustrated, the overhead housing assembly 804 includes the user interface 136. The user interface 136 may include the display 140 configured to display information (e.g., real-time operation data) related to operation of the UV disinfection system 100. For example, the display 140 may display showing an activation status of the UV light source 102 (e.g., on/off), a timer with elapsed time from UV light source 102 activation, estimated dynamic countdown clock for target dosage, actual dosage estimation, cumulative use tracking, or any other suitable metric for the overhead housing assembly 804 of the UV disinfection system 100. In some embodiments, the overhead housing assembly 804 may output the information related to operation of the UV disinfection system 100 to the mobile app 144 (e.g. shown in FIG. 3A) via communication circuitry 142 (e.g., Bluetooth circuitry, or any other suitable wireless protocol). Moreover, the display 140 may include a touchscreen such that the user may control operation of the overhead housing assembly 804 via the display 140. For example, the user may activate the UV light source 102 via the touchscreen. However, in another embodiment, operation of the overhead housing assembly 804 may be controlled via the mobile app 144 using a mobile phone, tablet, desktop computer, or any other suitable device.

Moreover, the overhead housing assembly 804 may include components configured to detect the information related to operation of the UV disinfection system 100 that is displayed via the display 140 and/or mobile app 144. For example, the overhead housing assembly 804 may include the infrared sensor 132 set forth above. The infrared sensor 132 may be configured to detect temperatures in a body temperature range (e.g., 95-105 degrees Fahrenheit) or within 10 degrees Fahrenheit of ambient temperature within the vehicle, which may indicate that a person is sitting in the vehicle. In some embodiments, the UV disinfection system 100 may deactivate or prevent activation of the UV light source 102 in response to the infrared sensor 132 detecting a temperature in the body temperature range. In some embodiments, the overhead housing assembly 804 may also include the motion sensor 134 and/or UV sensor 114 configured to provide additional data (e.g., motion data, distance data) for determining whether a person is sitting within the vehicle 800 (e.g., shown in FIG. 8). In some embodiments, the overhead housing assembly 804 may determine whether to deactivate or prevent activation of the UV light source 102 based at least in part on a combination of data from the infrared sensor 132, the motion sensor 134, and/or the UV sensor 114. For example, an ambient temperature inside of the vehicle 800 may be 100 degrees Fahrenheit (i.e., within the body temperature range), which would generally cause the overhead housing assembly 804 to deactivate or prevent activation of the UV light source 102 based on data from the infrared sensor 132. However, based on additional data from the motion sensor and/or the UV sensor 114 which is calibrated based on the installed configuration (or recalibrated by the user to account for car seats, or other aftermarket installed fixtures upon any surface within the vehicle), the overhead housing assembly 804 may determine that a person is not sitting within the vehicle 800 and maintain/allow operation of the UV light source 102.

Figure 10:
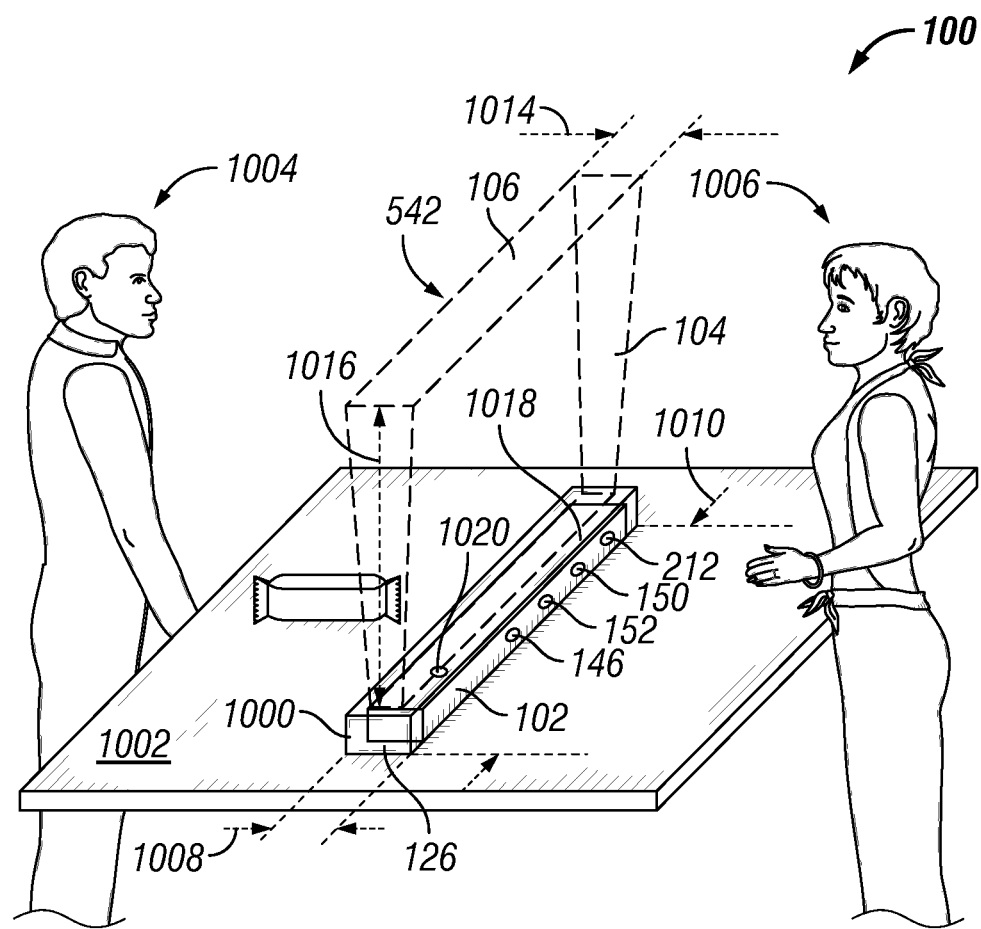
FIG. 10 illustrates a perspective view of an embedded UV disinfection system disposed in a retail space, in accordance with one or more embodiments of the disclosure.

FIG. 10 illustrates a perspective view of the UV disinfection system 100 disposed in a retail space, in accordance with one or more embodiments of the disclosure. The UV disinfection system 100 may include the UV light source 102 disposed within a base (e.g., housing 1000) of the UV disinfection system 100. The UV light source is configured to emit UV light 104 in a target volume 542 to at least partially inactivate an airborne pathogen exposed to the emitted UV light 104 in the target volume 542. The UV light source 102 may be configured to emit the UV light 104 along a path corresponding to the target volume 542. In the illustrated embodiment, the path of the UV light may be substantially normal to the housing 1000 for substantially the length 1010 and width 1008 of the housing 1000. In some embodiment, the width 1008 of the housing 1000 may be narrow relative to the length 1010 of the housing 1000 such that the UV light source 102 may be configured to output a narrow beam of UV light 104. In some embodiments, the UV light source 102 may be configured to output a 0.5-12 inch narrow UV light beam 104. That is, the UV light 104 may have a light beam width 1014 of 0.5-12 inches at the target location 106.

The UV disinfection system 100 may include a beam shaping mechanism 1018 (e.g., one or more reflectors disposed in the housing 1000, a slot disposed above or in the housing 1000, etc.) configured to shape the path of the emitted UV light 104 so that the UV light is confined to a selected light beam width 1014 for at least a selected height above or distance 1016 from the housing 1000. The UV light source 102 may be configured to output the UV light beams 104 at an output power sufficient to inactivate airborne pathogens passing through the narrow UV light beam 104 up to the selected distance 1016 (e.g., a distance to the target location 106 for the UV light) corresponding to a breathing zone for adjacent individuals. However, in some embodiments, the breathing zone may extend up to 5 feet, 10 feet, or to any other suitable distance. Further, as set forth above, the UV light source 102 may be configured to emit the UV light beam 104 at a mean peak wavelength range between 200-280 nanometers. However, the mean peak wavelength range may alternatively be between 200-250 nanometers, 200-220 nanometers, or any other suitable range. Further, the UV light source 102 may be configured to emit the UV light 104 at 1-120 millijoules/cm2 for at least the selected distance 1016 corresponding to the target location 106 and/or the target volume 542.

The UV disinfection system 100 may also include the visible light source 126 configured to emit the visible light 148 indicating that the UV light source 102 is active. For example, the visible light source 126 may be configured to emit a visible light indicating that the UV light source 102 is active. In some embodiments, the visible light source 126 is configured to output different colors based on a status of the embedded UV disinfection system 100. For example, the visible light source 126 may be configured to output a red light indicating that the embedded UV disinfection system 100 is inactive. Moreover, the pathogen disinfection system 100 may include other components such as the speaker device 146, the air freshener 150, and/or the tilt sensor 212 set forth above.

As illustrated, the UV light source 102 and the visible light source 126 may be embedded within the housing 1000. The housing 1000 may be at least partially UV-transparent such that the UV light may pass through a portion of the housing 1000. Moreover, the length 1010 of the housing 1000 may be selected length based at least in part on a desired length of coverage for the UV disinfection system 100. In the illustrated embodiment, the housing 1000 is positioned on top of a retail counter 1002 such that UV light beams 104 from the UV light source 102 may at least partially inactivate the airborne pathogens passing through the air between customers 1004 and workers 1006. Accordingly, the desired length may be a length of the counter, a length of the breathing zone, or any other suitable length for at least partially inactivate the airborne pathogens passing through the air between customers 1004 and workers 1006. Moreover, the UV light source 102 may be configured to operate (e.g., emit the UV light 104) in the presence of people, without any direct exposure to the people. For example, the customer 1004 and the worker 1006 may stand next to the retail counter 1002 with the housing 1000 without being directly exposed to the emitted UV light 104. Moreover, in some embodiments, the UV light source 102 and/or the visible light source 126 may be embedded within an embodiment of the retail counter 1002 having the material, which is at least partially UV-transparent, set forth above.

The pathogen disinfection system 100 may include a first motion sensor 1020 configured to detect when an object or human being (e.g., customer 1004 or worker 1006) has moved into the UV light path and to send a first signal in response to detecting such a movement. Further, the pathogen disinfection system 100 may include a proximity sensor 1022 configured to detect when a human being (e.g., customer 1004 or worker 1006) is present within a given distance from the housing 1000 in a particular direction and to send a second signal in response to detecting such a presence. In some embodiments, the proximity sensor 1022 may be a second motion sensor or a temperature sensor. The controller 110 (e.g., shown in FIG. 1) of the UV disinfection system 100 may be configured to activate the UV light source 102 after receiving the first signal and deactivating the UV light source 102 after receiving the second signal. In some embodiments, the controller 110 may be configured to activate the UV light source 102 with a time delay ranging from 0.1 to 10 seconds from receiving the first signal.

Figure 11:
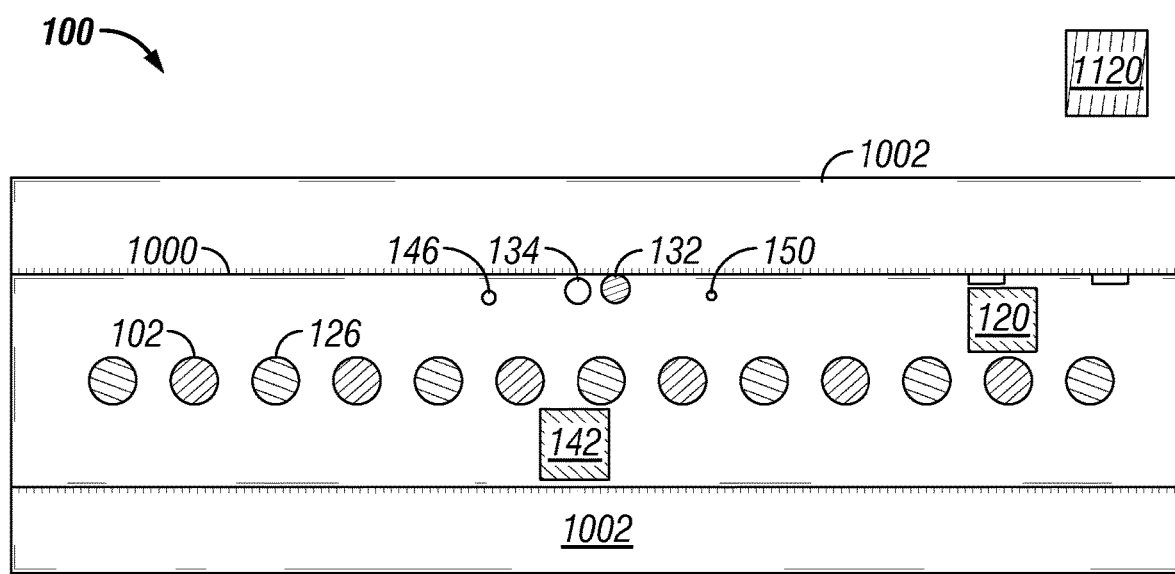
FIG. 11 illustrates a cross-sectional view of the embedded UV disinfection system of FIG. 11 disposed in the counter of the retail space, in accordance with one or more embodiments of the disclosure.

FIG. 11 illustrates a cross-sectional view of the UV disinfection system 100 of FIG. 11 disposed in the housing 1000, that is at least partially UV-transparent, on the retail counter 1002, in accordance with one or more embodiments of the disclosure. As set forth above, the UV light source 102 and the visible light source 126 may be disposed within the housing 1000 of the UV disinfection system 100. The housing 1000 may be configured to house other components of the embedded UV disinfection system 100. For example, the housing 1000 may house a sensor (e.g., the motion sensor 134, the infrared sensor 132, etc.) configured to detect people within the vicinity of the UV disinfection system 100. For example, the UV disinfection system 100 may include the infrared sensor 132 configured to detect temperatures within body temperature range (e.g., 95-105 degrees Fahrenheit) or over 10 degrees Fahrenheit above ambient or room temperature and up to a preset distance (e.g., fifteen feet) from the UV disinfection system 100. In response to detecting a temperature within the range, the UV disinfection system 100 may be configured to activate the UV light source 102 and may maintain operation of the UV light source 102 so long as a person is detected within the vicinity of the UV disinfection system 100. However, if the sensor fails to detect a person proximate the UV disinfection system 100, the UV disinfection system 100 may be configured to deactivate the UV light source 102. In some embodiments, the UV disinfection system 100 may include a shut-off delay instruction configured to delay deactivation of the UV light source 102 for shut-off delay period (e.g., 10 seconds) after the sensor fails to detect a person proximate the embedded UV disinfection system 100. In some embodiments, the shut-off delay period may be five minutes, ten minutes, or any suitable amount of time.

In some embodiments, the housing 1000, that is at least partially UV-transparent, may also be configured to house the speaker device 146 for outputting audio cues. For example, the speaker device 146 may be configured to output a warning sound when body temperature and/or motion is detected in a path of the UV light 104 emitted by the UV light source 102. The warning sound may be configured to deter customers 1004 and workers 1006 (e.g., shown in FIG. 10) from crossing over the UV light source 102. In another example, the housing 1000 may be configured to house the air freshener device 150 configured to output a scented aroma and/or a neutralizing agent in response to activation of the UV light source 102. The scented aroma may include a release timed hypoallergenic fragrance to provide olfactory confirmation of active operation of the embedded UV disinfection system 100. That is, a smell from the fragrance may indicate to customers 1004 and workers 1006 that the embedded UV disinfection system 100 is actively disinfecting such that the air quality proximate the housing 1000 is at least partially hygienic.

Moreover, the housing 1000 may also be configured to house the memory 120 of the UV disinfection system 100. The memory 120 may be configured to store operational data (e.g., cumulative use, elapsed time, etc.) for the UV disinfection system 100. Communication circuitry 142 (e.g., Bluetooth, WiFi, or LAN) may be secured within the housing 1000 to provide a connection to the mobile app 144 (e.g., shown in FIG. 3). Using the communication circuitry 142, the operational data may be uploaded to the mobile app 144, such that a user may remotely access the operational data. The mobile app 144 may be configured to store the operational data such that the hourly, daily, monthly, and annual operational data may be retrieved for analysis. In some embodiments, the mobile app 144 may include dose monitoring for workers 1006. Accordingly, the UV disinfection system 100 may include dose monitoring devices 1102 for the workers 1006 to wear on their person. The dose monitoring device 1102 may track exposure to UV light 104 emitted from the UV light source 102 and output exposure data to the mobile app 144.

Figure 12:
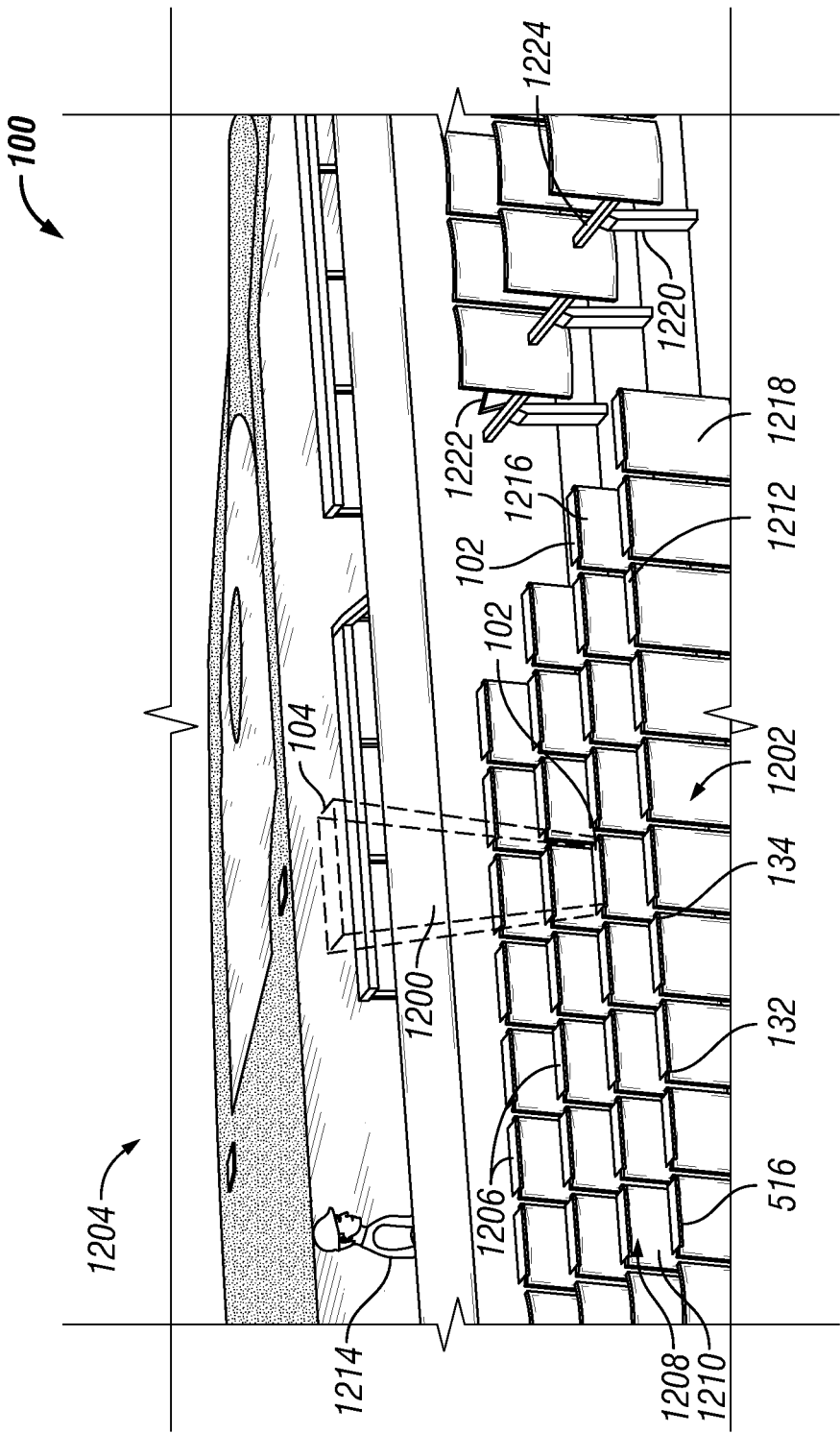
FIG. 12 illustrates a perspective view of an UV disinfection system for providing a disinfecting light curtain between seating arrangements in a public space, in accordance with one or more embodiments of the disclosure.

FIG. 12 illustrates a perspective view of an UV disinfection system 100 for providing a disinfecting light curtain 1200 between seats in a public space, in accordance with one or more embodiments of the disclosure. For example, the UV disinfection system 100 may provide the disinfecting light curtain 1200 between adjacent seats 1202 in an arena 1204 for hosting seated events (e.g., concerts, basketball games, churches, classrooms, auditoriums, theaters, live audience studios, etc.). In the illustrated embodiment, the UV disinfection system includes a mountable housing 1206 configured to attach to a portion of the seat 1202 in the arena 1204. In particular, the mountable housing 1206 is configured to mount to a top portion 1208 of a backrest 1210 of the seat 1202. The mountable housing 1206 may include fastening features 516 such as clamps, adhesives, or any other suitable fastening features 516 for securing the mountable housing 1206 to the seat. In some embodiments, the housing 1206 may be embedded within the top portions 1208 of a backrest 1210 of the seat 1202 and may include any suitable fastening features 516 for securing the mountable housing 1206 within the backrest 1210 of the seat 1202. In another embodiment, the housing 1206 may be placed atop a seating surface 1222 of a vacant the seat 1202, on an arm rest 1224, or to any suitable portion of the seat 1202.

Moreover, the UV light source 102 may be secured to the mountable housing 1206. In some embodiments, mountable housing 1206 includes a non-UV light reflecting, material 1212 that is at least partially UV-transparent. The UV light source 102 may be disposed within the material 1212. Having the material 1212 may protect the UV light source 102 from potential damage due to collisions, rain, etc. Moreover, as set forth above, the UV light source 102 is configured to emit UV light beams 104 to at least partially inactivate an airborne pathogen passing by the mountable housing 1206. Specifically, the UV light source 102 may be configured to output a narrow beam of UV light 104 (e.g., 1-3 inch narrow beam) to at least partially inactivate an airborne pathogen passing above the mountable housing 1206. The UV light source 102 may be configured to output the UV light beams 104 at an output power sufficient to inactivate airborne pathogens passing through the narrow UV light beam 104. Further, as set forth above, the UV light source 102 may be configured to emit the UV light beam 104 at a mean peak wavelength between 200-280 nanometers. Alternatively, the mean peak wavelength range may be between 200-250 nanometers, 200-220 nanometers, or any other suitable range.

In some embodiments, the UV disinfection system 100 is configured to activate the UV light source 102 in response to the seat 1202 corresponding to the UV disinfection system 100 being occupied by a patron 1214. The UV light source 102 is configured to operate (e.g., emit the UV light 104) in the presence of the patron, without any direct exposure to the patron or others. Moreover, the UV disinfection system 100 may include sensors (e.g., IR sensor 132, motion sensor 134, a pressure sensor 1220, etc.) to determine whether the patron 1214 is occupying the seat 1202 or in the vicinity. In some embodiments, the UV disinfection system 100 may be configured to automatically deactivate the UV light source 102 in response to the patron 1214 leaving the seat 1202 or the vicinity. However, the UV disinfection system 100 may include a timer configured to delay deactivation of the UV light source 102 for a predetermined amount of time (e.g., 8-10 seconds) after the UV disinfection system 100 detects that the patron 1214 left the seat 1202 or the vicinity. Moreover, the UV disinfection system 100 may include a tilt sensor configured to cause automatic deactivation the UV light source 102 in response to the UV disinfection system 100 being tilted. For example, in response to the backrest 1210 seat 1202 of a first seat 1216 being forced backward such that the UV light source 102 is directed toward a second seat 1218 positioned behind the first seat 1216, the UV disinfection system 100 may be configured to shut down the UV light source 102. Moreover, the UV disinfection system 100 may include any other suitable component set forth above.

Figure 13:
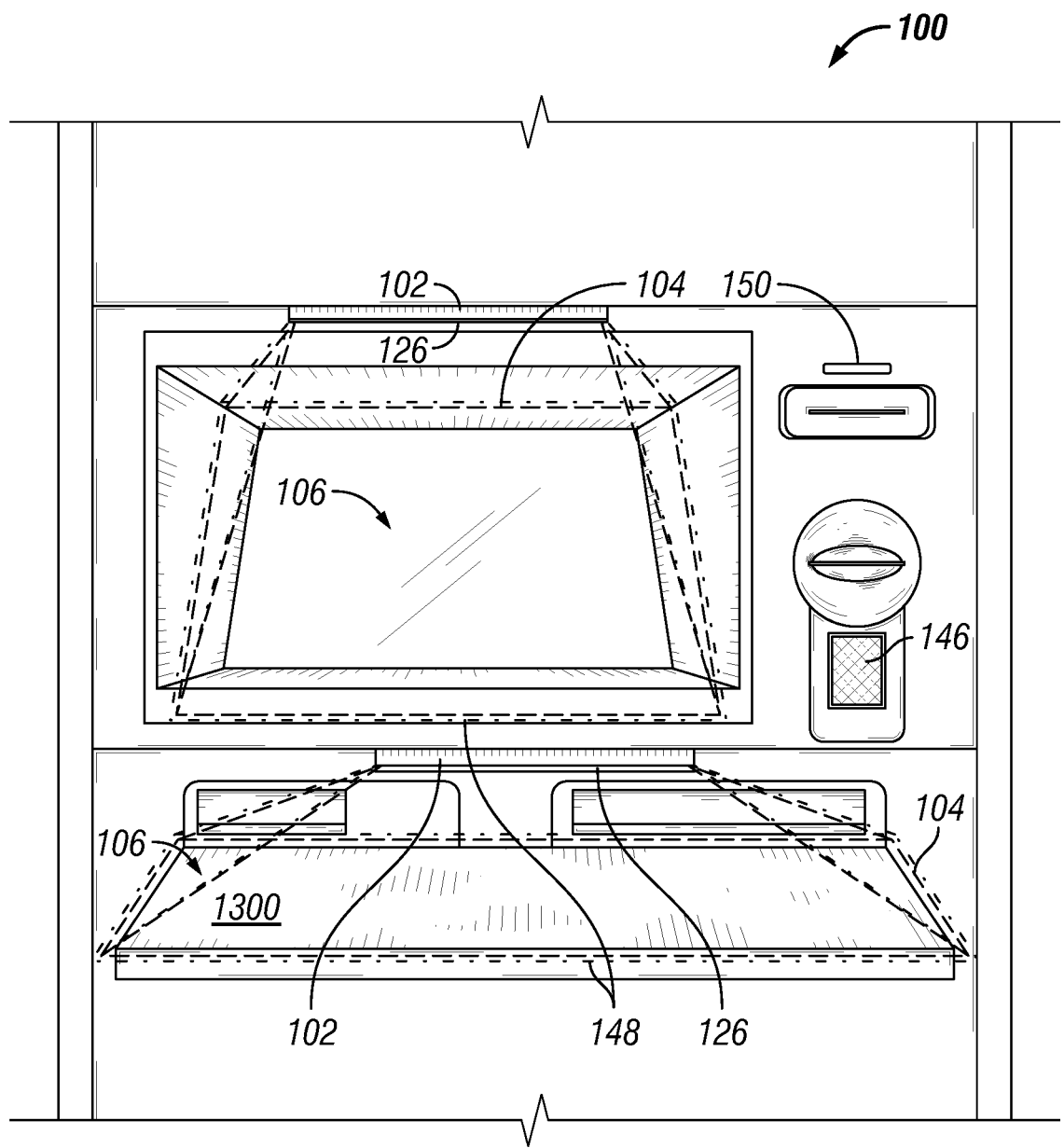
FIG. 13 illustrates a perspective view of the UV disinfection system for an automated teller machine (ATM) keypad, in accordance with one or more embodiments of the disclosure.

FIG. 13 illustrates a perspective view of the UV disinfection system 100 for an automated teller machine (ATM) keypad 1300, in accordance with one or more embodiments of the disclosure. In the illustrated embodiment, the UV disinfection system 100 includes UV light sources 102 configured to emit UV light 104 toward the target locations 106. As illustrated, the target location 106 includes the keypad 1300 of an ATM. In some embodiments, the UV light source 102 may be configured to emit UV light 104 toward any keypad or touchscreen operated in a public space (e.g. grocery store), including money/paper deposits and commonly touched surfaces. As set forth above, the UV light source 102 is configured to emit UV light 104 at a mean peak wavelength between 200-280 nanometers toward the target location 106 to at least partially inactivate airborne and surface-deposited pathogens at the target location 106. Alternatively, the mean peak wavelength range may be between 200-250 nanometers, 200-220 nanometers, or any other suitable range. The UV light source 102 may be configured to provide a target dosage of the UV light 104 to the target location 106 to achieve inactivation of the pathogens on the target location 106. In the illustrated embodiment, the target dosage may include 1-50 millijoule/cm$^2$ of exposure of the target location 106 to the UV light 104. The UV light source 102 may be configured output the UV light 104 at a power sufficient to provide the target dosage to the keypad in 3-30 seconds. However, the duration of the disinfection cycle for providing the target dosage may be adjusted based on a type of material of the target location 106. For example, a target location 106 having a porous material or surface roughness may have a disinfection cycle of up to 90 seconds.

The UV disinfection system 100 may also include the visible light source 126 for providing a visual indication of a status of the UV disinfection system 100. For example, the visible light source 126 may output visible light 148 having a first color (e.g., red) indicating that he UV disinfection system 100 is active and output a second color (e.g., green) indicating that the target location 106 (e.g., keypad) has been disinfected and is ready for use. Moreover, the UV disinfection system 100 may include the speaker device 146 for providing audio cues indicating the status of the UV disinfection system 100. Further, the UV disinfection system 100 may include any other suitable component (e.g., the air freshener 150) set forth above.

Figure 14:
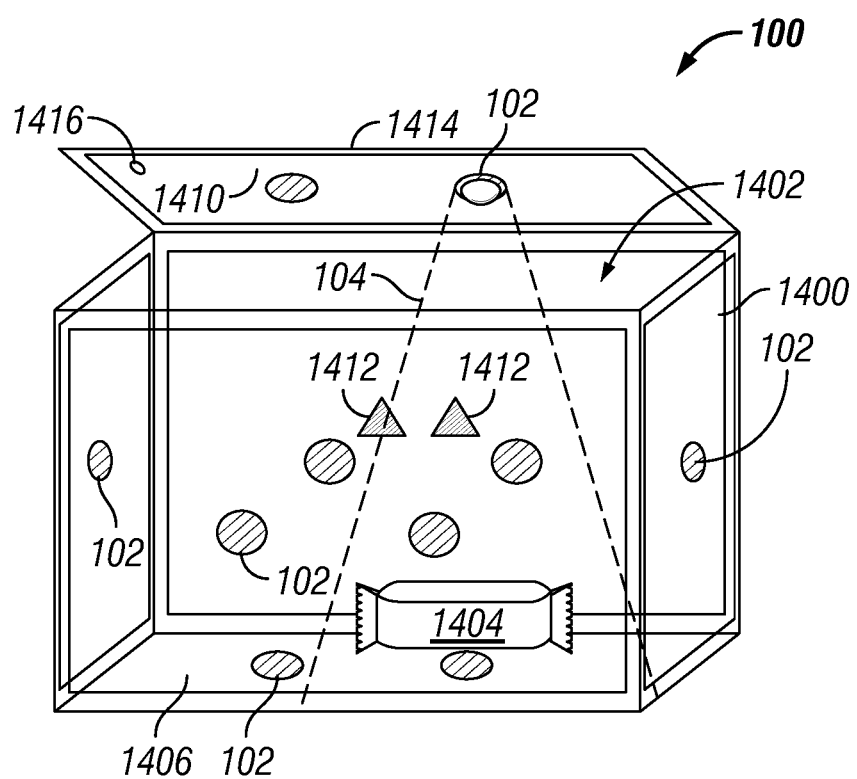
FIG. 14 illustrates a perspective view of a UV disinfection system having a portable compartment for disinfecting objects, in accordance with one or more embodiments of the disclosure.

FIG. 14 illustrates a perspective view of a UV disinfection system 100 having a portable housing 1400 with an internal compartment 1402 for disinfecting objects, in accordance with one or more embodiments of the disclosure. As illustrated, the UV disinfection system 100 includes a portable housing 1400 having an internal compartment 1402. The UV disinfection system 100 may include a plurality of UV light sources 102 disposed within the internal compartment 1402.

In some embodiments, the internal compartment 1402 includes the plurality of UV light sources 102 arranged to provide simultaneous three-dimensional UV light 104 within the internal compartment 1402. For example, an object 1404 (e.g., candy bar, mobile device 200, credit cards, keys, money, etc.) may be inserted into the internal compartment 1402 for disinfection. The plurality of UV light sources 102 may be disposed on internal bottom 1406, side 1408, and top 1410 walls of the internal compartment 1402 such that the simultaneous three-dimensional UV light 104 is output into the internal compartment 1402 to at least partially inactivate pathogens on the corresponding bottom, side, and top surface portions of the object 1404.

The UV light source 102 is configured to output the UV light 104 during a disinfection cycle to at least partially inactivate pathogens disposed within the air and surfaces in internal compartment 1402. In some embodiments, the disinfection cycle may be set via user interface 136 (e.g., shown in FIG. 1). For example, using the user interface 136, the user may set the disinfection cycle to a duration of five seconds. In some embodiments, the user interface 136 may include options to set the duration of the disinfection cycle to any duration within the range of 5-120 seconds.

Moreover, the portable housing 1400 may include a lid 1414 that may be opened to provide access to the internal compartment 1402. The UV disinfection system 100 may be configured to prevent activation of the plurality of UV light sources 102 when the lid 1414 is in the open position. The UV disinfection system 100 may include a sensor 1416 configured detect whether a door or lid 1414 into the internal compartment 1402 is closed or open. Further, the UV disinfection system 100 may include any other suitable component set forth above.

Accordingly, the preceding description provides a UV disinfection system configured to emit UV light to at least partially inactivate pathogens exposed to the emitted UV light. The systems, methods, and apparatus may include any of the various features disclosed herein, including one or more of the following statements.

Statement 1A. A pathogen disinfection apparatus may comprise an ultraviolet (UV) light source configured to emit UV light toward a target location to at least partially inactivate pathogens exposed to the emitted UV light in the path of the emitted light and a surface of the target location, the UV light having a mean peak wavelength between 200-280 nanometers; a distance sensor configured to determine a distance between the UV light source and the target location; and dosimetry circuitry configured to monitor a dose of the UV light at the target location in real-time based at least in part on an intensity of the UV light and the distance between the UV light source and the target location.

Statement 2A. The pathogen disinfection system of statement 1A, wherein the UV light having a mean peak wavelength between 200-280 nanometers is configured to at least partially inactivate the Covid-19 SARS-CoV-2 coronavirus.

Statement 3A. The pathogen disinfection system of statement 1A, wherein the UV light source is configured to emit the UV light to provide a target dosage of 1-120 millijoules/cm2 to the target location, the target location being between 5-300 cm from the UV light source.

Statement 4A. The pathogen disinfection system of statement 1A, further comprising a visible light source configured to emit visible light, the visible light source configured to activate when the UV light source is activated to indicate that the UV light source is active and the apparatus is in a disinfection mode.

Statement 5A. The pathogen disinfection system of statement 4A, wherein the UV light source configured to emit the UV light with a power draw of 0.1-150 watts toward the target location, and wherein the visible light source is configured to emit the visible light with a power draw of 0.1-150 watts toward the target location.

Statement 6A. The pathogen disinfection system of statement 1A, wherein the distance sensor comprises a UV sensor configured to receive the UV light reflected from the target location to determine the distance between the UV light source and the target location Statement 7A. A pathogen disinfection system may comprise a UV light source configured to emit UV light toward a target location to at least partially inactivate pathogens on the target location, the UV light having a mean peak wavelength between 200-280 nanometers; a visible light source configured to emit visible light; and a circuit configured to power the UV light source and the visible light source, wherein the circuit activates both the UV light source and visible light source in a disinfection mode.

Statement 8A. The pathogen disinfection system of statement 7A, wherein UV light source is configured to emit UV light with a power draw of 0.1-150 watts toward a target location and the visible light source is configured to emit visible light with a power draw of 0.1-150 watts.

Statement 9A. The pathogen disinfection system of statement 7A, wherein the UV light source and the visible light source are secured to a lighting fixture, wherein the lighting fixture is disposable facing the target location.

Statement 10A. The pathogen disinfection system of statement 7A, wherein the visible light source is configured to emit the visible light at a wavelength between 380-700 nanometers.

Statement 11A. The pathogen disinfection system of statement 7A, further comprising a motion sensor configured to detect movement inside of a safety area bounding a travel path of the UV light and output a shut-down or an activation signal.

Statement 12A. The pathogen disinfection system of statement 7A, wherein the circuit comprises a delay switch configured to delay activation of the disinfection mode for at least 5 seconds from receiving user input to activate the disinfection mode.

Statement 13A. The pathogen disinfection system of statement 7A, wherein the target location includes one or more of the group comprising: a table; a seating arrangement; and an area wherein people may congregate.

Statement 14A. The pathogen disinfection system of statement 7A, wherein the UV light source is secured within an interior of a vehicle and configured to at least partially inactivate pathogens exposed to the emitted UV light in the path of the emitted light and a surface of the target location within the interior of the vehicle.

Statement 15A. The pathogen disinfection system of statement 7A, wherein the UV light comprises a light beam width of 0.5-12 inches at the target location Statement 16A. A pathogen disinfection system may comprise a UV light source configured to emit UV light toward a target location to at least partially inactivate pathogens exposed to the emitted UV light in the path of the emitted light and a surface of the target location at the target location, the UV light having a mean peak wavelength between 200-280 nanometers; a temperature sensor configured to monitor a temperature at the target location, wherein the temperature sensor is configured to output a deactivation signal in response to detecting a temperature within a predetermined temperature range at the target location; and a circuit configured to deactivate the UV light source in response to receiving the deactivation signal from the temperature sensor.

Statement 17A. The pathogen disinfection system of statement 16A, wherein the predetermined temperature range includes temperatures between 95-105 degrees Fahrenheit or over 10 degrees Fahrenheit above ambient or room temperature.

Statement 18A. The pathogen disinfection system of statement 16A, further comprising a UV detector, wherein the UV detector comprises a first surface that is selected from the materials comprising at least in part photochromic pigments, dyes, or other colorants that have the property of changing color under the UV light having a mean peak wavelength between 200-280 nanometers.

Statement 19A. The pathogen disinfection system of statement 16A, further comprising a UV detector, wherein the UV detector is configured to provide the indication in response to exposure to a target dosage of 1-120 millijoules/cm2 of the UV light for at least 10 seconds, wherein the indication includes a surface of the UV detector changing colors from a first color to a second color and/or third color.

Statement 20A. The pathogen disinfection system of statement 19A, wherein the UV detector is configured to revert from the third color to the second color, or second color to the first color at least 10 seconds after exposure to the UV light ceases.

Statement 1B. A pathogen disinfection system may comprise a base having a selected length; a pathogen disinfection apparatus including at least one ultraviolet (UV) light source disposed in the base and configured to emit UV light having a mean peak wavelength between 200-280 nanometer in a target volume, in a path substantially normal to the base for substantially the length of the base, to at least partially inactivate pathogens exposed to the emitted UV light in the path of the emitted light in the target volume; a beam shaping mechanism such as one or more reflectors disposed in the base or a slot disposed above or in the base and configured to shape the path of the emitted UV light so that the UV light path is confined to a selected width for at least a selected height or distance from the base; a first motion sensor configured to detect when an object or human being has moved into the UV light path and to send a first signal in response to detecting such a movement; a proximity sensor configured to detect when a human being is present within a given distance from the base in a particular direction and to send a second signal in response to detecting such a presence; and a controller to activate the UV light source after receiving the first signal and deactivating the UV light source after receiving the second signal.

Statement 2B. The pathogen disinfection system of statement 1B, wherein the base is mounted to or otherwise placed upon a portion of a chair such as the back, seating surface, or arm rest.

Statement 3B. A pathogen disinfection system of statement 1B, wherein the base is mounted to or otherwise placed upon a counter or other flat-topped surface.

Statement 4B. The pathogen disinfection system of statement 1B, wherein the UV light source is configured to emit 1-120 millijoules/cm$^2$ of UV light for at least a distance corresponding to the selected height or distance from the base.

Statement 5B. The pathogen disinfection system of statement 1B, further comprising a visible light source configured to emit visible light, the visible light source configured to activate when the UV light source is activated to indicate that the UV light source is active and the apparatus is in a disinfection mode.

Statement 6B. The pathogen disinfection system of statement 1B, wherein the proximity sensor is a second motion sensor or a temperature sensor.

Statement 7B. The pathogen disinfection system of statement 1B, further including data port configured to transmit data to and receive commands from a controller.

Statement 8B. The pathogen disinfection system of statement 7B, wherein the controller comprises a processor and an application having processor executable instructions configured for sending signals for operating the UV light source, the proximity sensor, and the motion sensor, and receiving data therefrom.

Statement 9B. The pathogen disinfection system of statement 8B, wherein the data includes operational data, diagnostics, and maintenance parameters.

Statement 10B. The pathogen disinfection system of statement 1B, wherein the base comprises a non-UV light reflecting, at least partially UV-transparent material configured to allow transmittance of the UV light emitted from the UV light source.

Statement 11B. The pathogen disinfection system of statement 1B, further comprising a speaker device configured to produce an audio output in response to activation of the UV light source, before, during, or after activation or deactivation of the UV light source, or some combination thereof.

Statement 12B. The pathogen disinfection system of statement 1B, further including an air freshener configured to output a scented aroma and/or a neutralizing agent in response to activation of the UV light source.

Statement 13B. The pathogen disinfection system of statement 1B, further including a tilt sensor configured to provide a tilt angle signal indicating a tilt angle of the pathogen disinfection apparatus, and wherein the controller is configured to receive the tilt angle signal and deactivate the UV light source in response to a maximum tilt angle having been exceeded.

Statement 1C. A pathogen disinfection fan system may comprise a fan having blades or other motive device to induce airflow in a particular direction; a motor coupled to the fan configured for rotating the fan blades or motive device to induce the airflow in the particular direction; a ceiling mount; a connecting member connecting the ceiling mount to the fan and motor; and a pathogen disinfection apparatus mounted to the connecting member, the apparatus including at least one ultraviolet (UV) light source configured to emit UV light having a mean peak wavelength between 200-280 nanometer in a target volume, in a substantially horizontal path substantially normal to the direction of the induced airflow to at least partially inactivate pathogens exposed to the emitted UV light in the path of the emitted light in the target volume.

Statement 2C. A pathogen disinfection fan system, as claimed in statement 1C, wherein the motor is configured to rotate the fan in either a first or a second rotational direction opposite to the first rotational direction.

Statement 3C. A pathogen disinfection fan system, as claimed in statement 2C, having a switch configured to activate the UV light source wherein the motor is configured to rotate in the first or the second rotational direction.

Statement 4C. A pathogen disinfection fan system, as claimed in statement 1C, wherein the motor is configured to cause the fan to induce a first downward air flow or second upward air flow.

Statement 5C. A pathogen disinfection fan system, as claimed in statement 4C, having a switch configured to activate the UV light source wherein the motor is configured to cause the fan to induce the first downward air flow or second upward air flow.

Statement 6C. A pathogen disinfection fan system, as claimed in statement 1C, further comprising: a temperature or motion sensor configured to detect a temperature or a motion in a volume below the fan and to provide an activation input signal to activate the UV light source in response to sensing a particular temperature or motion in the volume below the fan.

Statement 7C. A pathogen disinfection fan system, as claimed in statement 1C, further comprising: a clock circuit; and a signal generator configured to generate a time signal indicating the times when the UV light source is active; a transmitter configured to transmit the time signal; and a recording device configured to receive the time signal and record the times during which the UV light source is active.

Statement 8C. A pathogen disinfection fan system, as claimed in statement 1C, wherein the recording device comprises a software application including processor executable instructions configured for operating the fan, the UV light and recording the times during which the UV light source is active.

Statement 9C. The pathogen disinfection system of statement 1C, further comprising a speaker device configured to produce an audio output in response to activation of the UV light source, before, during, or after activation or deactivation of the UV light source, or some combination thereof.

Statement 10C. The pathogen disinfection system of statement 1C, further including an air freshener configured to output a scented aroma and/or a neutralizing agent in response to activation of the UV light source.

Statement 11C. The pathogen disinfection system of statement 1C, further including a tilt sensor configured to detect a tilt orientation of the pathogen disinfection apparatus, and wherein the UV light source is configured to deactivate in response to a maximum tilt angle having been exceeded.

Statement 12C. The pathogen disinfection system of statement 1C, further comprising a speaker device configured to produce an audio output in response to activation of the UV light source, before, during, or after activation or deactivation of the UV light source, or some combination thereof.

Statement 13C. The pathogen disinfection system of statement 1C, further including a housing or baffling to further direct the induced airflow.

Statement 14C. The pathogen disinfection system of statement 1C, further comprising a user interface configured to the UV light source in response to user input.

Statement 15C. The pathogen disinfection system of statement 1C, wherein the UV light source emits a light beam spread between 0-180 degrees.

Statement 1D. A mobile communication device may comprise a pathogen disinfection apparatus including an ultraviolet (UV) light source configured to emit UV light having a mean peak wavelength between 200-280 nanometers toward a target location to at least partially inactivate pathogens exposed to the emitted UV light in the path of the emitted light and a surface of the target location; and an application including processor executable instructions configured to generate signals to control the pathogen disinfection apparatus.

Statement 2D. A mobile communication device, as claimed in statement 1D, wherein: the pathogen disinfection apparatus further comprises a visible light source configured to emit visible light; and the application includes processor executable instructions configured to generate signals for communication to the visible light source to operate the visible light source to activate the visible light source when the UV light source is active.

Statement 3D. A mobile communication device, as claimed in statement 1D, wherein: the pathogen disinfection apparatus further comprises a temperature or motion sensor configured to provide a deactivation input signal to the application upon sensing a particular temperature or motion within a light beam emitted from the UV light source; and the application includes processor executable instructions configured to generate a signal for communication to the UV light source to deactivate the UV light source in response to receiving the deactivation input signal from the temperature or motion sensor.

Statement 4D. A mobile communication device, as claimed in statement 1D, wherein: the pathogen disinfection apparatus further comprises a distance sensor configured to determine a distance between the UV light source and the target location and to generate a distance input signal.

Statement 5D. A mobile communication device, as claimed in statement 4D, wherein: the distance sensor comprises a UV sensor which determines distance from the target surface based upon sensing the UV light reflected from the target location to generate the distance input signal.

Statement 6D. A mobile communication device, as claimed in statement 4D, wherein: the pathogen disinfection apparatus further comprises a dosimetry circuit or algorithm configured to receive the distance input signal and generate a cumulative dose signal indicating a cumulative dose of UV light received at the target location in real-time based at least upon the distance input signal and an intensity of the UV light emitted at the UV light source.

Statement 7D. A mobile communication device, as claimed in statement 6D, wherein the application further comprises processor executable instructions configured to receive the cumulative dose signal and to send a deactivation signal to the UV light source when the cumulative dose signal indicates that a target dose has been achieved.

Statement 8D. A mobile communication device, as claimed in statement 1D, wherein the mobile communication device includes a speaker mechanism and the application further comprises processor executable instructions configured to activate the speaker mechanism to emit an audible sound, before, during, or after activation or deactivation of the UV light source, or some combination thereof.

Statement 9D. A mobile communication device, as claimed in statement 1D, wherein the application further comprises computer executable instructions to operate the UV light source in response to a user input.

Statement 10D. A mobile communication device, as claimed in statement 9D, wherein the application further comprises computer executable instructions to generate a visual interface to allow a user to provide the user input.

Statement 11D. A mobile communication device, as claimed in statement 1D, wherein: the mobile communication device includes a tilt sensor to a tilt sensor configured to provide a tilt angle signal indicating a tilt angle of the mobile communication device; and the application includes processor executable instructions configured to receive the tilt angle signal from the mobile communication device and to generate a deactivation signal for deactivating the UV light source in response to a maximum tilt angle having been exceeded.

Statement 1E. An accessory for a mobile communication device, the mobile communication device having an exterior housing and a processor, the accessory may comprise: a pathogen disinfection apparatus mountable to the exterior housing of the mobile communication device, the pathogen disinfection apparatus including an ultraviolet (UV) light source configured to emit UV light having a mean peak wavelength between 200-280 nanometers toward a target location to at least partially inactivate pathogens exposed to the emitted UV light in the path of the emitted light and a surface of the target location; and an application for downloading to the mobile communication device, the application including processor executable instructions configured to generate signals to control the pathogen disinfection apparatus, including to operate the UV light source.

Statement 2E. An accessory for a mobile communication device, as claimed in statement 1E, wherein: the pathogen disinfection apparatus further comprises a visible light source configured to emit visible light; and the application includes processor executable instructions configured to generate signals for communication to the visible light source to operate the visible light source to activate the visible light source when the UV light source is active.

Statement 3E. An accessory for a mobile communication device, as claimed in statement 1E, wherein: the pathogen disinfection apparatus further comprises a temperature or motion sensor configured to provide a deactivation input signal to the application upon sensing a particular temperature or motion within a light beam emitted from the UV light source; and the application includes processor executable instructions configured to generate a signal for communication to the UV light source to deactivate the UV light source in response to receiving the deactivation input signal from the temperature or motion sensor.

Statement 4E. An accessory for a mobile communication device, as claimed in statement 1E, wherein: the pathogen disinfection apparatus further comprises a distance sensor configured to determine a distance between the UV light source and the target location and to generate a distance input signal.

Statement 5E. An accessory for a mobile communication device, as claimed in statement 4E, wherein: the distance sensor comprises a UV sensor which determines distance from the target surface based upon sensing the UV light reflected from the target location to generate the distance input signal.

Statement 6E. An accessory for a mobile communication device, as claimed in statement 4E, wherein: the pathogen disinfection apparatus further comprises a dosimetry circuit or algorithm configured to receive the distance input signal and generate a cumulative dose signal indicating a cumulative dose of UV light received at the target location in real-time based at least upon the distance input signal and an intensity of the UV light emitted at the UV light source.

Statement 7E. An accessory for a mobile communication device, as claimed in statement 6E, wherein the application further comprises processor executable instructions configured to receive the cumulative dose signal and to send a deactivation signal to the UV light source when the cumulative dose signal indicates that a target dose has been achieved.

Statement 8E. An accessory for a mobile communication device, as claimed in statement 1E, wherein the mobile communication device includes a speaker mechanism and the application further comprises processor executable instructions configured to activate the speaker mechanism to emit an audible sound before, during, or after activation or deactivation of the UV light source, or some combination thereof.

Statement 9E. An accessory for a mobile communication device, as claimed in statement 1E, wherein the application further comprises computer executable instructions to operate the UV light source in response to a user input.

Statement 10E. An accessory for a mobile communication device, as claimed in statement 1E, wherein the application further comprises computer executable instructions to generate a visual interface to allow a user to provide the user input.

Statement 11E. An accessory for a mobile communication device, as claimed in statement 1E, wherein: the pathogen disinfection apparatus further comprises a tilt sensor to provide a tilt angle signal indicating a tilt angle of the mobile communication device; and the application includes processor executable instructions configured to monitor the tilt angle signal and generate a deactivation signal for communication to the UV light source to deactivate the UV light source in response to a maximum tile angle having been exceeded.

Statement 12E. An accessory for a mobile communication device, as claimed in statement 1E, wherein the target location comprises a keypad, touchscreen, or any surface disposed in a public space.

Statement 1F. A pathogen disinfection system comprising: a light array; a proximity sensor; and a controller configured to send and receive signals to the light array and proximity sensor; wherein the light array comprises a plurality of ultraviolet (UV) light sources and a plurality of visible light sources; wherein each of the UV light sources and the visible light sources are configured to produce an individual light beam having an individual volume between the emitter and an individual target surface area located at a given distance away from the individual sources; wherein each UV light emitter is configured to emit ultraviolet light having a mean peak wavelength between 200-280 nanometer to at least partially inactivate pathogens exposed to the emitted UV light in the path between the respective UV light source and its target surface area; wherein the plurality of UV light sources of the array are collectively configured to produce a collective light beam having a collective volume between the array and a collective target surface area; and wherein the plurality of visible light emitters are configured to collectively illuminate the collective target area to indicate that the UV light emitters are active and the system is in a disinfection mode; wherein the controller is configured to send a first signal to the light array to activate the light array and a second signal to the light array to deactivate the light array; and wherein the proximity sensor is configured to detect the presence of a human being within a given safety volume greater than or equal to the target volume and to emit a motion signal to the controller to deactivate the light array upon detecting the presence of a human being.

Statement 2F. The pathogen disinfection system of statement 1F, wherein at least one light emitter of the array is individually configurable to be pointed towards its target surface area.

Statement 3F. The pathogen disinfection system of statement 1F, wherein the controller includes a deactivation circuit or algorithm to deactivate the array when the deactivation circuit or algorithm determines that a target dose of UV light has been achieved on the collective target surface area.

Statement 4F. The pathogen disinfection system of statement 3F, wherein the deactivation circuit or algorithm determines that a target dose of UV light has been achieved on the collective target surface area based upon at least in part on an intensity of the UV light and the distance between each UV light emitter and its individual target surface area.

Statement 5F. The pathogen disinfection system of statement 1F, wherein the UV light is configured to provide a target dosage of 1-120 millijoules/cm$^2$ to the target location to at least partially inactivate the Covid-19 SARS-CoV-2 coronavirus.

Statement 6F. The pathogen disinfection system of statement 1F, further comprising a speaker device configured to produce an audio output at least when the UV light emitters are active and the system is in disinfection mode.

Statement 7F. The pathogen disinfection system of statement 1F, wherein the controller further comprises a user interface configured to operate the array in response to user input.

Statement 8F. The pathogen disinfection system of statement 1F, wherein the collective target surface includes one or more of the group comprising: a table; a seating arrangement; and an area wherein people may congregate.

Statement 9F. The pathogen disinfection system of statement 1F, wherein the collective target surface comprises a keypad, touchscreen, or any surface disposed in a public space.

Statement 10F. The pathogen disinfection system of statement 1F, wherein the proximity sensor is a temperature sensor configured to monitor a temperature in a predetermined range within the target volume.

Statement 11F. The pathogen disinfection system of statement 1F, wherein the proximity sensor is the predetermined range is between 95-105 degrees Fahrenheit or over 10 degrees Fahrenheit above ambient or room temperature within the target volume.

Statement 12F. The pathogen disinfection system of statement 1F, wherein the proximity sensor is a motion sensor configured to detect when an object or human being has moved into the UV light path within the target volume.

Statement 13F. The pathogen disinfection system of statement 1F, further comprising a UV detector, wherein the UV detector comprises a first surface that is selected from the materials comprising at least in part photochromic pigments, dyes, or other colorants that have the property of changing color under the UV light having a mean peak wavelength between 200-280 nanometers.

Statement 14F. The pathogen disinfection system of statement 12F, further comprising a UV detector, wherein the UV detector is configured to provide the indication in response to exposure to a target dosage of 1-120 millijoules/cm$^2$ of the UV light for at least 10 seconds, wherein the indication includes a surface of the UV detector changing colors from a first color to a second color and/or third color.

Statement 15F. The pathogen disinfection system of statement 13F, wherein the UV detector is configured to revert from the third color to the second color, or second color to the first color at least 10 seconds after exposure to the UV light ceases.

Statement 16F. The pathogen disinfection system of statement 1F, wherein the controller comprises a processor and an application having processor executable instructions.

In the above description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belong. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof.

Although several embodiments of inventive concepts have been disclosed in the foregoing specification, it is understood that many modifications and other embodiments of inventive concepts will come to mind to which inventive concepts pertain, having the benefit of teachings presented in the foregoing description and associated drawings. It is thus understood that inventive concepts are not limited to the specific embodiments disclosed hereinabove, and that many modifications and other embodiments are intended to be included within the scope of the appended claims. It is further envisioned that features from one embodiment may be combined or used with the features from a different embodiment(s) described herein. Moreover, although specific terms are employed herein, as well as in the claims which follow, they are used only in a generic and descriptive sense, and not for the purposes of limiting the described inventive concepts, nor the claims which follow. The entire disclosure of each patent and patent publication cited herein is incorporated by reference herein in its entirety, as if each such patent or publication were individually incorporated by reference herein. Various features and/or potential advantages of inventive concepts are set forth in the following claims.

What is claimed is:

1. A pathogen disinfection system, comprising:
a base having a selected length;
a pathogen disinfection apparatus including at least one ultraviolet (UV) light source disposed in the base and configured to emit UV light having a mean peak wavelength between 200-280 nanometers in a path substantially normal to the base for substantially the length of the base, the emitted UV light forming a disinfecting light curtain to at least partially inactivate airborne pathogens passing through the disinfecting light curtain, wherein the disinfecting light curtain is configured to separate a breathing zone for a first individual from another individual to at least partially inactivate airborne pathogens passing through the air between the individuals;
a beam shaping mechanism comprising one or more reflectors disposed in the base or a slot defined in the base, wherein the beam shaping mechanism is configured to shape the path of the emitted UV light forming the disinfecting light curtain so that the disinfecting light curtain is confined to a selected width for at least a selected height or distance from the base, wherein the selected width is between a maximum of 0.5-12 inches, and wherein the selected height or distance from the base is between a minimum of 3-10 feet;
a first motion sensor configured to detect when an object or human being is in the UV light path and to send a first signal in response to detecting the object or human being in the UV light path;
a proximity sensor configured to detect when a human being is present within a given distance from the base in a particular direction and to send a second signal in response to detecting such a presence; and
a controller to activate the UV light source in response to receiving the second signal and to deactivate the UV light source in response to receiving the first signal.

2. The pathogen disinfection system of claim 1, wherein the base is mounted to or otherwise placed upon a portion of a chair, wherein the portion of the chair comprises a back, a seating surface, an arm rest, or some combination thereof.

3. A pathogen disinfection system of claim 1, wherein the base is mounted to or otherwise placed upon a counter or other flat-topped surface.

4. The pathogen disinfection system of claim 1, wherein the UV light source is configured to emit 1-120 millijoules/$cm^2$ of UV light for at least a distance corresponding to the selected height or distance from the base.

5. The pathogen disinfection system of claim 1, further comprising a visible light source configured to emit visible light, the visible light source configured to activate when the UV light source is activated to indicate that the UV light source is active and the apparatus is in a disinfection mode.

6. The pathogen disinfection system of claim 1, wherein the proximity sensor is a second motion sensor or a temperature sensor.

7. The pathogen disinfection system of claim 1, further including data port configured to transmit data to and receive commands from the controller.

8. The pathogen disinfection system of claim 7, wherein the controller comprises a processor and an application having processor executable instructions configured for sending signals for operating the UV light source, the proximity sensor, and the motion sensor, and receiving data therefrom.

9. The pathogen disinfection system of claim 8, wherein the data includes operational data, diagnostics, and maintenance parameters.

10. The pathogen disinfection system of claim 1, wherein the base comprises a non-UV light reflecting, at least partially UV-transparent material configured to allow transmittance of the UV light emitted from the UV light source.

11. The pathogen disinfection system of claim 1, further comprising a speaker device configured to produce an audio output in response to activation of the UV light source, before, during, or after activation or deactivation of the UV light source, or some combination thereof.

12. The pathogen disinfection system of claim 1, further including an air freshener configured to output a scented aroma and/or a neutralizing agent in response to activation of the UV light source.

13. The pathogen disinfection system of claim 1, further including a tilt sensor configured to provide a tilt angle signal indicating a tilt angle of the pathogen disinfection apparatus, and wherein the controller is configured to receive the tilt angle signal and deactivate the UV light source in response to a maximum tilt angle having been exceeded.

14. The pathogen disinfection system of claim 1, wherein the at least one UV light source is configured to emit the UV light at a mean peak wavelength between 210-220 nanometers in the target volume.

15. A pathogen disinfection system, comprising:
a base having a selected length;
a pathogen disinfection apparatus including at least one ultraviolet (UV) light source disposed in the base and configured to emit UV light having a mean peak wavelength between 200-280 nanometers in a path substantially normal to the base for substantially the length of the base, the emitted UV light forming a disinfecting light curtain to at least partially inactivate airborne pathogens passing through the disinfecting light curtain, wherein the disinfecting light curtain is configured to separate a breathing zone for a first individual from another individual to at least partially inactivate airborne pathogens passing through the air between the individuals;
a beam shaping mechanism comprising one or more reflectors disposed in the base or a slot defined in the base, wherein the beam shaping mechanism is configured to shape the path of the emitted UV light forming the disinfecting light curtain so that the disinfecting light curtain is confined to a selected width for at least a selected height or distance from the base, wherein the selected width is between a maximum of 0.5-12 inches, and wherein the selected height or distance from the base is between a minimum of 2-5 feet;
a first motion sensor configured to detect when an object or human being is in the UV light path and to send a first signal in response to detecting the object or human being in the UV light path;
a proximity sensor configured to detect when a human being is present within a given distance from the base in a particular direction and to send a second signal in response to detecting such a presence; and
a controller to activate the UV light source in response to receiving the second signal and to deactivate the UV light source in response to receiving the first signal.

16. The pathogen disinfection system of claim 15, wherein the beam shaping mechanism further comprises one or more reflectors disposed in the base.

17. A pathogen disinfection system, comprising:
a retail counter;
a pathogen disinfection apparatus including at least one ultraviolet (UV) light source embedded in the retail counter and configured to emit UV light at a mean peak power between 5-100 watts and a mean peak wavelength between 200-280 nanometer in a path substantially normal to the retail counter for substantially the length of the retail counter, the emitted UV light forming a disinfecting light curtain to at least partially inactivate airborne pathogens passing through the disinfecting light curtain, wherein the disinfecting light curtain is configured to separate a breathing zone for a first individual on one side of the counter from another individual on the other side of the counter to at least partially inactivate airborne pathogens passing through the air between the individuals; and
a beam shaping mechanism configured to shape the path of the emitted UV light forming the disinfecting light curtain so that the disinfecting light curtain is confined to a selected width for at least a selected height or distance from the retail counter.

18. The pathogen disinfection system of claim 17, wherein the beam shaping mechanism comprises one or more reflectors embedded within the retail counter.

19. The pathogen disinfection system of claim 17, wherein the beam shaping mechanism comprises a slot disposed above the UV light source.

20. The pathogen disinfection system of claim 17, wherein the selected width is between a maximum of 0.5-12 inches wide, and wherein the selected height or distance from the retail counter is between a minimum of 2-5 feet.

* * * * *